US010066266B2

(12) United States Patent
Hakonarson et al.

(10) Patent No.: US 10,066,266 B2
(45) Date of Patent: Sep. 4, 2018

(54) GENETIC ALTERATIONS ON CHROMOSOMES 21Q, 6Q AND 15Q AND METHODS OF USE THEREOF FOR THE DIAGNOSIS AND TREATMENT OF TYPE 1 DIABETES

(71) Applicant: The Children's Hospital of Philadelphia, Philadelphia, PA (US)

(72) Inventors: Hakon Hakonarson, Malvern, PA (US); Struan Frederick Airth Grant, Swarthmore, PA (US); Jonathan Paul Bradfield, San Diego, CA (US); Constantin Polychronakos, Quebec (CA); Hui-Qi Qu, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 142 days.

(21) Appl. No.: 14/628,147

(22) Filed: Feb. 20, 2015

(65) Prior Publication Data

US 2015/0299793 A1    Oct. 22, 2015

Related U.S. Application Data

(63) Continuation of application No. 12/947,564, filed on Nov. 16, 2010, now abandoned, which is a continuation-in-part of application No. PCT/US2009/044356, filed on May 18, 2009.

(60) Provisional application No. 61/054,040, filed on May 16, 2008.

(51) Int. Cl.
| | |
|---|---|
| C07H 21/02 | (2006.01) |
| C07H 21/04 | (2006.01) |
| C12Q 1/6883 | (2018.01) |
| A61K 38/28 | (2006.01) |
| C12N 15/113 | (2010.01) |

(52) U.S. Cl.
CPC ............ *C12Q 1/6883* (2013.01); *A61K 38/28* (2013.01); *C12N 15/113* (2013.01); *C12Q 2535/131* (2013.01); *C12Q 2600/106* (2013.01); *C12Q 2600/136* (2013.01); *C12Q 2600/156* (2013.01); *C12Q 2600/172* (2013.01); *Y10T 436/143333* (2015.01)

(58) Field of Classification Search
CPC ..... A61K 31/713; A61K 38/28; C12N 15/113
See application file for complete search history.

(56) References Cited

U.S. PATENT DOCUMENTS

| | | | |
|---|---|---|---|
| 7,205,106 B1 | 4/2007 | Mirel et al. | |
| 7,312,196 B2 * | 12/2007 | L'Italien | A61K 9/0014 424/400 |

FOREIGN PATENT DOCUMENTS

| | | |
|---|---|---|
| WO | 2003010335 | 2/2003 |
| WO | 2004045543 | 6/2004 |
| WO | 2006010146 | 1/2006 |

OTHER PUBLICATIONS

Reference SNP (refSNP) Cluster Report: rs3757247 [online], <URL:http://www.ncbi.nlm.nih.gov/projecl s/SNP/snp_ref. cgi?rs=3757247>.
Todd. J.A., et al., Robust associations of four new chromosome regions from genome-wide analyses of type 1 diabetes, Nat Genet., 2007, 857-64, 39(7).
Lowe, C.E., et al., Large-scale genetic fine mapping and genotype-phenotype associates implicate polymorphism in the IL2RA region in type 1 diabetes, Nat Genet., 2000, 1074-1082, 39.
Qu, H.Q., et al., Toward further mapping of the association between the IL2RA locus and type 1 diabetes, Diabetes. 2007, 1174-6, 56(4).
Smyth, D.J., et al., A genome-wide association study of nonsynonymous SNPs identifies a type 1 diabetes locus in the interferon-induced helicase (IFIH1) region, Nat Genet., 2006, 617-9, 38(6).
Ueda, H., et al., Association of the T-cell regulatory gene CTLA4 with susceptibility to autoimmune disease, Nature, 2003, 506-11, 423(6939).
Gunderson, K.L., et al., A genome-wide scalable SNP genotyping assay using microarray technology, Nat Genet., 2005, 549-54, 37(5).
Diao, J., et al., Glucose-regulated glucagon secretion requires insulin receptor expression in pancreatic alpha-cells, J Biol Chem., 2005, 33487-96, 280(39).
Hakonarson, H., et al., A genome-wide association study identifies KIAA0350 as a type 1 diabetes gene, Nature, 2007, 591-4, 448(7153).
Probe Reagents for Functional Genomics. Bead microarray (bead) probe for *Homo sapiens* variation 2 rs2358994. Developed for genotyping. Reagent is available from Illumina. IN: NCBI website Jan. 11, 2007. (Retrieved on Sep. 15, 2009) Retrieved from the Internet: <URL:http://www.ncbi.nih.gov/genome/probe/reports/probereport.cgi?uid=7451377>.
Hiromine, et al., Trinucleotide repeats of programmed cell death-1 gene are associated with susceptibility to type 1 diabetes mellitus, Metabolism Clin Exp., 2007, 505-509. [ABSTRACT].
Grant, S.F., et al., Follow-up analysis of genome-wide association data identifies novel loci for type 1 diabetes, Diabetes, 2009, 290-5, 58(1).
Wang et al., High-throughput SNP genotyping by single-tube PCR with Tm-shift primers, BioTechniques, 2005, 885-892, 39(6).
USCS Genome Browser (NCBI36/hg18) Assembly, Genome Browser website, Mar. 2006, Retrieved from internet: <http://www.genome.uscs.edu/cgi-bin/hgTracks>.
Nucleic Acids, Linkers and Primers, NEB Catalog, 1998/1999, 121 and 284.

\* cited by examiner

*Primary Examiner* — Amy H Bowman
(74) *Attorney, Agent, or Firm* — Kathleen D. Rigaut; Dann, Dorfman, Herrell & Skillman

(57) ABSTRACT

Compositions and methods for the detection and treatment of T1D are provided.

5 Claims, 3 Drawing Sheets

Specification includes a Sequence Listing.

BACH2-related protein-protein interaction network of differentially expressed genes (DEG) for T1D is created by IPA software.

EDG7/LPAR3-related protein-protein interaction network of differentially expressed genes (DEG) for T1D is created by IPA software.

```
                        SEQUENCE LISTING

<160> NUMBER OF SEQ ID NOS: 255

<210> SEQ ID NO 1
<211> LENGTH: 2492
<212> TYPE: DNA
<213> ORGANISM: Homo Sapiens

<400> SEQUENCE: 1
gtgcaggcga gcttcttggc ctaagggcag gaagagatgg cagcggggga gacgcagctc      60
tacgccaagg tctccaacaa gctcaagagc cgcagcagcc cctcgctcct ggagcccctc     120
ctggccatgg gcttcccggt gcacaccgcg ctgaaagcgt tggcagccac ggggaggaag     180
acggcggagg aggccttggc ctggctgcat gatcattgca atgacccttc cctagacgac     240
cccatccccc aggagtatgc ccttttcctc tgtccaacgg ggcccctgct ggaaaaactt     300
caagagttct ggagagagag caagcgccag tgtgcaaaga acagagctca tgaggtcttc     360
ccacacgtga cactctgtga cttcttcacg tgtgaagacc agaaggtgga atgcctgtac     420
gaggcgctga gagagctgga agacaggctc ctgggctcct tccccacggc cgtgcctctg     480
gctctccact cctccatcag ctacctcggc ttcttcgtca gtggcagccc cgcagacgtc     540
atccgggaat tcgccatgac cttcgccacg gaagcatctc tcttagcagg cacttccgtt     600
tcccgcttct ggattttcag ccaggtgcct ggacatggcc ctaacctgag gctgagcaat     660
ttaactagag cctccttcgt gagccactac atccttcaaa aatactgctc cgtgaagcct     720
```

```
tgcaccaaac agctgcatct gaccttggcc cacaagttct acccccacca ccagaggacg      780
ctggagcagc tggccagagc catcccctg ggccacagct gccagtggac cgcagcactc       840
tactcccgag acatgcgctt tgtgcactac cagaccctga gagccctatt ccagtacaaa      900
ccccagaact ggatgagct gacgctaagt cctggtgact acatctttgt ggaccccacg       960
cagcaggacg aagccagcga gggctgggtg attgggatct cacagcggac gggctgccgg     1020
ggcttcctgc cggaaaacta cacgatcga gccagtgagt ctgacacgtg ggtgaagcac      1080
aggatgtaca ccttcagtct agccacagac ctgaactcca aaaggatgg tgaagccagc      1140 agcagatgca gcggggaatt tcttccacaa acggcaagga gtcttagcag cttacaggcc     1200
ttgcaggcta ccgttgcaag gaagagcgtg ctggtggttc gccacgggga gagagtggat     1260
cagatcttcg ggaaggcatg gctgcagcaa tgctccactc ctgatgggaa atactacagg     1320
ccagacctga atttccctg cagtctgcca agacggagtc gtgggatcaa gactttgaa       1380 aacgatcccc cattatcatc gtgtggcatt ttccagtcca gaattgcagg gacgcgcta      1440 ctggacagtg gtatcagaat cagctctgtg tttgcctccc cagccctccg ctgtgtgcag     1500
acggccaaac tcatcctgga agaactcaaa ctggagaaaa aaatcaagat acgagtggaa     1560
cctggaatct ttgaatggac aaaatgggaa gctggcaaaa ccaccccaac cctcatgagc     1620
ctggaagagc tgaaagaggc aaatttcaac attgacactg attacaggcc cgcgtttccc     1680
ctgtccgccc tcatgccggc cgagagctac caggagtaca tggacaggtg cacggcgagc     1740
atggtgcaaa tcgtcaacac ctgtccacag gacacgggtg tcatcctaat tgtgagtcac     1800
ggctccactc tggactcctg cacgcggcca ctgctcgggc tgccgccccg ggaatgtggg     1860
gattttgccc aactcgtgag aaagatccct tccctgggca tgtgcttctg tgaagaaaat     1920
aaagaggaag gaaaatggga gttggtgaac ccaccggtga agaccctgac ccacggggcg     1980
aacgcagcat taactggag gaactggatc tcaggcaact gagagccacg gtgatgttgt      2040
cataacctca gagtggagag gcagaaacca tgtgcagagg ctgggagatg ctgctgtttc     2100
cagaggcgtc ttagtctcac ccaatgtgat ttgtagaagc acgagacgca cttttatatc     2160
ccggaatatt tccctccggc tttcgccttt gtaactccca tctgtggacc catcgtccac     2220
cagcccagct gcggggagca cagggcaggt ggctgggtga ggatgccgcc ctgcagcatg     2280
tacaccgagt gtctgcagct ggggacacaa ctgcccggga ctctaacttc aggaattaa      2340 agactcacca cacgaagg atctaaccac ttcatttcc atggtctaat cattaaattc         2400
ccaatcgttt tttcttttc tgggtccatc actctttagc catatccaca tgggctaaaa      2460
caggtgtaat agtcaataaa atggtcccag aa                                   2492
```

<210> SEQ ID NO 2
<211> LENGTH: 7656
<212> TYPE: DNA
<213> ORGANISM: Homo Sapiens

<400> SEQUENCE: 2

```
ctccctccct cttcccccctt ccctctccc tgcagccgcg tccacactgc gccgcccggg       60
cagcccagag cgcggcgcgc acgggcaccg gcggcgagtg ccgcggccac tgcccctccc     120 gggacccccct gtacgccgtc cgcgccgtcc agggtcacac cggcgacgga acccgccggc    180
agcaattagc cagcatcccg gggtcggccc ccagaagcat tccccggccc aggacgagga    240
tgaacaggac aggcgaggca caaagtcgca actgaacttt ttagaaacat tatttgtgtg    300
```

```
tgtatgtgtg tagcagggga gaatgagctg atgccgaggg tccagccacc ccgcctctgc    360
ctcctcctcc ccctgccgcc gctgccctcg cagacgcgcg cgcacacacg gcacttgggc    420
cgggtttccg cgctccgtcc ccccgtttgg atggggtttt tcatttccga aggaggcaca    480
gcccgcggag cgtctctgaag ggctggagcc ccaagttact cctcgccagc gccggccgcc    540
cgctgtcact cgcgctggcc ggccggggga agggaccgc acgccgggct tgttgtgga      600 aatcccggtt acctggctta tacccacac catggataac ttattggact ttgcctgaaa     660
ggagtcatta gtgacattgg atatttgacc gtcttggcca caggtttttc agaatgaatg    720
gaagatcatg cagcatgagt ctccaccgga catcgggaac cccacagggg cctaggatgg    780
tcagtggtca tcacattcct gccatccgag cccactccgg gactcctggc ccctcgccct    840
gtggcagcac atcgagtccc actatggcaa gccttgctaa caacctccat ctcaagatgc    900
cctcaggagg agggatggct cctcagaaca acgtggctga gagccgcatc catctgcctg    960
ccttaagccc caggagacaa atgctcacca atgggaagcc gcgattccag gtcacccagg   1020
ctggaggcat gtcagggtca catactttaa agccaaagca gcaggagttt ggaagccctt   1080
ttcctccaaa tcctgggaaa ggggctcttg gctttgggcc tcagtgcaag tccattggaa   1140
aaggcagctg caacaatcta gtggtcacca gcagtcccat gatggttcag cgactgggac   1200
tcatttcacc tccagcaagc caggtctcta cagcatgcaa ccagatcagt cctagcttac   1260
agagggcaat gaatgcagcc aacctgaata tacctccttc agataccagg tcccttattt   1320
cgcgtgagtc tttggcgtcc acgaccttga gtctgacgga aagtcagtcg gcctcaagca   1380
tgaagcagga gtggtcccag ggctacaggg ccctcccttc gctctccaac cacggctctc   1440
agaatggcct tgatctaggg gatctcctta gccttcctcc cgggacatcc atgtccagca   1500
atagtgtctc taactcatta ccatcctacc tttttggcac ggaaagtagc cactctcctt   1560
accctagtcc tcggcactca tccaccaggt cccactcggc ccgctccaag aagagagcgc   1620
tgtccttgtc ccgctgtcc gatggcatcg ggatagattt caataccatc atccgcacgt    1680
cgcccacgtc cttggtggcc tacatcaacg ggtcgagggc ttcgccggcc aacctgtccc   1740
cgcagccgga ggtctacggg catttcctgg gcgtgcgcgg cagctgcatt ccccagccgc   1800
gcccggtgcc cggcagccag aagggcgtgc tggtggcccc tggaggcctg gcgctgccgg   1860
cctacggcga ggacggggcc ctggagcacg agcgcatgca acagctggag cacggcggcc   1920
tgcagccagg cctggtcaac cacatggtgg tgcagcatgg cctgccgggc cccgacagcc   1980
agtcggccgg cctgttcaag accgaacgcc tggaggagtt cccgggcagc accgtagacc   2040 tacccccgc gcctccgctc cctcctctgc cgccgccccc aggcccccca cccccttacc    2100
atgcccatgc gcaccttcac cacccggagc tcgggcccca cgcccagcag ctggccttgc   2160
cccaggccac cctggacgac gacggggaga tggacggcat cggggcaag cattgctgcc    2220 gctggatcga ctgcagcgcc ctgtacgacc agcaggagga gctcgtgcgg cacatcgaga   2280
aggtccacat cgaccagcgc aaaggggagg acttcacttg cttctgggcc ggttgccctc   2340
gaagatacaa gccccttcaac gcccgctata aactgctgat ccacatgaga gtccactctg   2400
gggagaagcc caacaagtgt acgtttgaag gttgcgagaa ggcctttttca aggcttgaaa   2460 atctcaagat ccacttgcgg agccacacag gcgagaagcc gtatttgtgc cagcatccgg   2520
gttgtcagaa ggccttcagt aactccagtg accgcgccaa acaccagcgg acgcatctgg   2580 acaccaaaacc ttatgcttgt caaattccag gatgtaccaa acgctacaca gacccaagtt  2640
ccctaagaaa gcatgtgaag gcacattctt ccaaagagca acaagcaagg aaaaagttgc    2700
```

```
ggtccagcac agagctccat ccagacctgc tcacagattg cctcaccgtg cagtccctgc   2760
agccggccac ttcccctaga gatgctgctg ctgaagggac cgtgggacgc tcccctggac   2820
ccgggcctga cctctattca gctcccattt tctccagcaa ttattcaagc cgaagtggaa   2880
cagctgctgg ggccgtacca cccccacatc ctgtcagtca cccttctcca ggacataatg   2940
tacaggggag ccctcacaac ccctcctccc agttacctcc actcacagct gtggacgcag   3000
gagctgagag gtttgcacct tctgctccat ctcctcacca catcagcccc cggagagttc   3060
cagctccttc ttcaatactg caaagaacac agcctcccta tacccagcag ccatcaggtt   3120
cacacctgaa gtcctatcag ccagaaacaa actcttcttt tcaaccaaat ggtatccatg   3180
tccatggatt ttatgggcag ctgcagaagt tctgtccccc acactacccc gattcccaga   3240
gaattgtgcc gcctgtcagc tcctgcagtg tggtgccttc gtttgaggac tgcctagtcc   3300
ctacatccat gggccaggcc agttttgatg ttttccacag agccttctcg actcactcgg   3360
gcattacagt gtatgattta ccttcaagtt cctcgagcct cttttgggag tctctccgca   3420
gcggggctga agatgctacc ttcttgcaga tcagcaccgt ggaccgctgt cctagccagc   3480
tctcctctgt ctacaccgaa ggctaaaagc tctcttggcc actcctgcac acccaggacc   3540
ttgatgttgc ttgccacctt ttgttttcgt actctcacag actgcttgag gaaggatgtc   3600
agcccaatca gcgggccctg cagagttact gatgttcttt cagaaggcag gactgaatgg   3660
cagagctagc tttgcaggaa tcattacagt tgctccttt tctctctggt tttcctggac   3720
tatgtgacca ggaggactgt cttttcaaag ggaatttaga gcctcactct cctggatacc   3780
tgttacttcc tggctgtcaa cccttaaagg accccagtga aatgatgtgc atatgaaaat   3840
gtagtttggg gatgactcta cctgaaaact ccaaacaggg aaaaagacct caattacgag   3900
aggcatagtg acctgcctca cctaatcctc acccttgctg ctcctgatgc aaagccaggc   3960
acaacaaggg aaatccatgt ccaaagcata gtgtggtctc aactcttaga aactccctgg   4020
gtttcccttt tctcttagcc acatgctaac cagttgcttc tcagtgtttc tcttcaatag   4080
aaaaataagg ttttatatgc cagcagccta tccttgtttt tgcattttaa agacttagtt   4140
atttatacgt attttaaaat gaaaaaaaaa tgtaaaggtc tgtgctttgg atggaaatca   4200
ttattattgt aatcacccca gctatagaca ttttgcacag ctgtggttct gcctggcccc   4260
acctctagca tgttagtttt gcagttagca aaggttacct gagggaaatg gagtgggcac   4320
ctcccgcacc aacagtcctg tagctggaac cttcctgagt tgactgttta gtaactccac   4380
ctcaaagact gtgttcaaag aaaaatgttg tttgactggt ttacccattg cctccactct   4440
ggtgctgcac ccagagaagt gccagatgtg agaactggga cagactgagt catgtgccag   4500
cttcccttgg aaaaccaaac ctagtgatac ttgacttcca gtgctcagat tttactaacg   4560
tttttcagga tatccactca tctgtctgtc tcttccctac acttctctcc accctctttt   4620
tgcatccctc ttaccctctt cctgactgtg gttcatatat ccccaccagc cgccattgtc   4680
tgatcatctt gggaaggtag aggtgacagt tctcgaaaag tctacagaaa gaggcaattc   4740
tttttctgag ttccagtttg aaggcctgga attttcacat agcacttggt cgaaaatatc   4800
aagcctaaat aggaagtcat tttctgtgac acctctacat agctattaca gatcctaagt   4860
cctagggcat cagctataaa aattggccag tcccaaagac acagtaagtt ctaacattct   4920
ggtactatca tatttcaagt attttttctc acttttaaa aatgttttc tgaacaaaag   4980 tgaaacaatg ccatttatca aactgagatc attacaatct tcaacaagac aactaaaaca   5040
```

```
gcttgatgtt agatgggatt ctgtgacagt ttgtatactg acaggtcctt ccagtctccc    5100
tccacagtcc cacaagcgga agtattctac ctgattccag agttcattcc aacatgcagt    5160
agaatgaggt gaatgaagaa ccaagtgtgg gttttgtttt cacagtgcac ttggtcaatc    5220
tagtttctct gagtagtggg ctgtattcta agaaaagctt tcacgtagac gtcaaagtct    5280
gcaaaagaga tgagttagcc actttaaaaa acctgctctg ctttacaaaa gatgcacacc    5340
aggcttcctt tacaagtgaa ctccaaggct gcttgtaaag taccaccctt cctgcagact    5400
ttgtgggtcg tgtcacttgg cctaaacaag tggcctaaca tatgcatgct cacagctagt    5460
agcatccctc atgcgtcctt tgtcatactc tggaaagaaa aaaactctgc tatcttcaga    5520
gaaaccatct attcatactt aaatatggaa gcctttacaa ggaactcaaa atacatttca    5580
tttcatttgt acaatgagaa aaaagatgaa aaggcaaggt tgttattgca gttgacattg    5640
tcagccctgc cttttggctt tatgtaattt aaaatagaaa gggggaagga ggacaagaca    5700
gaagctcaac tttagaaacc atggacatca cctccctctt tgagaggagc tgcttgtgaa    5760
ccaggctcca gtcttcctgt ggcctctcac agtaaccctg cccctttctt acctcacagg    5820
ggcaagaggg actctaaaga gggcgtaagc aatagaggca cctgcagccc tccttcctca    5880
gcaggaaatc aatgtggagc cccagaggga cattttatct cagagagagc atgctggcca    5940
caggacccag tgcagccctg cttccgcac cgtgggtctt tcctgatagc tgcaggcttg    6000
agattgcagc ctcaggatag gacacgttca gatgccttcc agactacaca cactatgctt    6060
agattcgaga gtctttcctg accttaaaat ttgtcccttg cttactttca cactgcagaa    6120
gatttatata tatattcatc attatttttg cagcagtaca agtggaaact tcaaaaaaat    6180
cattcccttt catgtcctgg tcttttttaag tcttgatatg taaccatttt cataaatgtc    6240
caaacagaga ttgtcattcc ccttaaaaac agaaacaaaa cacaaaacta gtgcttgtga    6300
aaacacacag cgcaaagaca attatcctat tgcattaaaa aaaaaatcag tctgcctaga    6360
gacatttcat tggctgcatt gtcttaattc cctaacgaaa ctgcatcaaa atgtcagttg    6420
taatttagcc tctgatcagc tgttaaatat tatttaaata tttacaggtc ctgtggggta    6480
tctcccatta cccatgtcgc cctcaaatta cataagcgat cataaaataa gaagaaaaaa    6540
aaaggtcttt agtagatcac agcagagtta ccactgataa gagtgttggc tttgttcagt    6600
tgtttctaaa ttaccagccg tcaagcacag tagcccctaa aaccaatttt gagcaaggat    6660
aaattcaact ccctcatctg agaaccttga cttttccagtt gccttgaagt attgggaata    6720
gtaactgtac attttcaatt taattatttg gtatttatt tgactgtctt ggccatgtca    6780
ttttatggaa gcatttttaa atagcacttt tgttagtgg tgtggaattt ctgcggttat    6840
tatttttttt ttttttttgca acagatgaag caaaaaaaaa aaagcactca ttggagaaat    6900
agtgagtgta aaaagagatt tattttgtac agacagcaaa gtatcctgtg taatgttgct    6960
gacataaagc actttggggg aaaaaagtgg aaatctgttt tccataaatc acacagactc    7020
ttgtacatag ttatatacac tcacgtagag aaatgaactg catatatcat actggatatg    7080
gggccgattt tactctagag gcacatctgg tgcttattgt cataaatctt ttaaagaatt    7140
aggtacactt ttttctatta atatgtatag ttttgtgatt tgtcacagtt atgtttcata    7200
taatcataag ttattttgtc ttgttcatga agtcctttt ttatgtcaaa agtaaaatga    7260
agggattgtg cacttggtac agaataaaac tggaaataga gaagacgccc tcctgcctaa    7320
aatcctcctt cagcctgtcg gtttaaaaca caatggcaac catcattgtt tgtttgtttg    7380
tttttttgtt ttgttttacc atcagcctct tacatactgg gaatggtaat tataattaaa    7440
```

-continued

| | | |
|---|---|---|
| ggcagatgat gcgggaggga atgttcaagt ccagctttaa aatgctgcat tgctttgggc | 7500 | |
| cagagctgta gcctggattt aattatagat atgaggagga aatggcagta aaatgaatg | 7560 | |
| tctccctgag tcctttacat gttgggagtg tccataaata aaacatgaag ttttatttca | 7620 | |
| tcagatttaa ttaaagcttt tatacatgtt aaaaaa | 7656 | |

<210> SEQ ID NO 3
<211> LENGTH: 5021
<212> TYPE: DNA
<213> ORGANISM: Homo Sapiens

<400> SEQUENCE: 3

| | | |
|---|---|---|
| cccgggggggg agagagccgg caggcggcgg cggtggtggc gggggcgatg cgccgcgccc | 60 | |
| ggccgcgcta ggtgagccgg caccgggagc gcgggccgcg gccatgggca ccctgggcaa | 120 | |
| ggcgagagag gctccgcgga aaccttccca tggctgcaga gctgcctcta aagcaagact | 180 | |
| agaggcaaag ccagccaaca gccccttccc ctcccatccc agcttggccc acatcaccca | 240 | |
| gttccgaatg atggtgtctc tgggacattt agccaaagga gccagcctgg acgatctcat | 300 | |
| tgacagctgc attcaatctt ttgatgcaga tggaaacctg tgtcgaagta accaactgtt | 360 | |
| gcaagtcatg ctgaccatgc accgaattgt catctcctct gcagaactgc tccaaaaagt | 420 | |
| tatcaccctc tataaggatg ctttggcaaa gaattcacca ggactttgcc tgaagatctg | 480 | |
| ttattttgta aggtattgga taacagaatt ctgggtcatg tttaaaatgg acgccagctt | 540 | |
| gacagacact atggaggagt ttcaggaact ggtgaaagct aagggtgagg agttacattg | 600 | |
| ccgcctgatt gacacaactc aaatcaatgc ccgtgactgg tccaggaaac ttactcaaag | 660 | |
| gataaaatca ataccagca agaaacggaa agtctccctg ctctttgacc atctggaacc | 720 | |
| agaagagcta tccgagcacc tcacctacct tgagttcaag tctttccgga ggatatcgtt | 780 | |
| ctctgattat cagaattacc ttgtaaatag ctgtgtgaag gaaaaccccca ccatggagcg | 840 | |
| atctattgct ctgtgcaacg gcatctccca gtgggtacaa ctgatggttc tcagccgccc | 900 | |
| cacgccgcag ctccgagcag aagtcttcat caagttcatc caggtggctc agaagctcca | 960 | |
| ccaactacag aacttcaata cactgatggc tgtgataggg gggctgtgtc acagctcaat | 1020 | |
| ctcgaggctc aaggagacaa gttcgcatgt cccacatgaa atcaataagg ttctcggtga | 1080 | |
| gatgactgag ctgctgtcct cctccagaaa ctacgacaat taccggcgag cctatggaga | 1140 | |
| gtgcaccgac ttcaagatcc ccattctggg tgtgcatctc aaggacctca tctcccctgta | 1200 | |
| tgaagccatg cctgactatc tggggacgg gaaagtgaac gtccataagc tactggccct | 1260 | |
| atacaatcat atcagtgaat tggtccagct gcaagaggtg gccccaccct tggaggctaa | 1320 | |
| caaggacttg gtacacttgc tgacgttatc cctggatctt tactacactg aggatgaaat | 1380 | |
| ctatgagctt tcctatgccc gggaaccaag gaaccacaga gctccaccac taacaccttc | 1440 | |
| aaagccacca gtagtagtgg actgggcttc tggagtgtct cccaaacctg atccaaaaac | 1500 | |
| cattagcaaa cacgtccaga ggatggtgga ttctgtcttc aagaactatg atcacgacca | 1560 | |
| ggatggatac atttctcagg aagaatttga aaagattgct gcgagttttc cattttcctt | 1620 | |
| ctgtgtgatg gacaaagaca gggaaggcct catcagcagg gatgagatca cagcctactt | 1680 | |
| catgagagcc agctcaatct attccaagct gggcctgggc tttcctcaca acttccaaga | 1740 | |
| gaccacctac ctgaagccca ctttttgtga caactgtgct ggattttctct ggggagtgat | 1800 | |
| caaacaagga tatcgatgta aagactgcgg gatgaactgt cacaaacaat gcaaagatct | 1860 | |

```
ggttgtgttt gagtgtaaga agcgagccaa gaacccagta gctcccacag agaacaacac   1920
ttctgtgggg ccagtgtcca acctttgctc attgggagcc aaagatctgc tccatgcacc   1980
tgaggaagga ccttttacat tccctaatgg ggaggctgtg gaacatggtg aggagagtaa   2040
ggatcggacc atcatgctga tgggagtgtc ctcacagaag atttctcttc ggctgaagag   2100
ggctgttgcc cacaaggcca cccagactga atcacagcct tggattggca gtgagggccc   2160
ttcaggtccc tttgtgctgt cttccccaag gaagacagcc caggatactc tatatgtgct   2220
tcccagtccc acctctccat gtcctagccc agtcttggtc agaaagcggg cttttgtcaa   2280
gtgggagaat aaagactccc tcataaaatc aaaggaggag ctccgtcacc tcagactgcc   2340
tacctaccaa gaactggaac aggaaataaa tactctgaaa gcagataatg atgccctaaa   2400
gatccaactg aaatatgcac agaagaaaat agaatccctc cagcttgaaa aaagcaatca   2460
tgtcttagct caaatggagc agggtgactg ttcttagccc agaaactaag tagcacaatc   2520
tgtagatgag tatagtgatc tcatttccta aactgtaatg cacagacctg aggaacttta   2580
cactgaccag ctttaaaaca gtactttaaa aggaaaagcc tgttactgtt tatttaccta   2640
aaagattcct aatgtgcagc actgttttct ctttcagtta gttgactcaa agggggaaaa   2700
ctaaagaatg caaaactttt gctattcata ccactgatgt tcatcaaaag tatgcgatct   2760
aaaacatgac tatcatttcc tgacaatggg gcatctcggt ggcctgcctg gctgattctt   2820
ccttaaaact aaaatctctg gaaaatggat ttgcttctta ccctgtgttt tctgcaaact   2880
gacttacttt gttccagcca agcttgcta  ataatagaaa actacccata ttccaaaagt   2940
agatttcctc tgtatcccag catactttgt gaacctggct ccttcttcac tacctcagat   3000
ctaatcaatt agtccatgta ccctccttcc tcactacagt cataacacat gagcatatct   3060
acctagaagc caatttctac tgatgtagcc acaactttt  agaggcctat taaacatgac   3120
gttatccaat tgcaggtcaa cttatagttg tagccttaca acttacaggc atcagaaaat   3180
aagtaatcaa attaggtacc tggaaacata gctattacca tctcatatta ctgtctaatt   3240
aaaataaaca taacgcaaac atgtttgtcc ttatatattc tacagtggat agaattagga   3300
attgatggct taaaaaaaaa agtctatgaa gagtctgttt aactcttcat gttccatctt   3360
tctcttctga agtaaactat tttgaaagtt ctcttttga  aatgaatttg tgcttaactg   3420
tcttcactat taatactatt tagaaataag ctaattggat cagtggctta aataatagct   3480
gactgtgtgt acatatgtat ataatatgta tatacaatat caggcatgca tgtggcttgg   3540
aattttgttt cctccataaa atgtggaagt gaattaaaca agttttagtc atttatacaa   3600
agtcacaaat ataagttca  gtttgtcaca agattaaatt gctcacaagg taaaattgta   3660
ttgtttggca aaatcacaag taacaatcct gtgagttttc tattatgaag gttaataata   3720
aatgggctca tttagttgcc tgggcaccta ttcacaaatt catttgtcag cctctttta   3780 gttctcttaa aaaaaaaaa  atcatatgat catttttctt tttgggggta cttagcttcc   3840
atgcctataa agtctggtac cagactgact tgaaattcat aaacaagttg tccaattgcc   3900
aagaatatgt taacaattaa aagttccaaa ctaaagccaa tagcaccaag tcttcataag   3960
aatacaaagt atacatacag tattgcttac ctggaggatt cagatcattt aggaattctc   4020
tttgatgaaa gatcagttcc catttgagtt cctccttgca ctgagtttta gtgatataga   4080
actagcttgt agttagtgtt tcattacatt ataaagaata gttttacaca cgtatttacc   4140
gttttccaaa tttaaactca gaaatacccca aagcaggcct gcttaagccc actacctggc   4200
atataaactt atagtaacac tttgttactt tcttttttaat aggacaagca tgagttagga   4260
```

```
caaactctaa aaattcatat tcttcactat tcttgttttc ctttgattga tatagaccaa      4320
agatggtgta ctctaatttt ttaaaacagt aatggaacac aattttttc attcttcctc       4380 ctctccattc gaagtaaaga tccccagtta gtttttatat aaataatcta tagggattca      4440
aaaggtgtca cagtccactt aattagtcaa attagcaatg gctaaacagt atcaagtact      4500
gcagaattta tcactgaaat ggataagagg aaatagttta gtcacaggtt tttacagtcc      4560
agcaagggcc aaagaggtat agtatacaag ttaatagtat ttgtgttgag caacatgggg      4620
ctagtgggat cacagaaatc tggaaaaaaa aaaaaaaagg ctttggctta tcaagcctag      4680
tgtaaatttc tgcatctcac acgactttag tttggccagg tatttatctg ccaaaacaag      4740
gacaaatctt gttgtattaa cagcagggtc acttctcatt ttctttgctg acttaccttt      4800
ttactgaccg ttgtgaattt ctgtctcaaa atgtataata tagaaatgca agaaaaaaac      4860
aaatgtacag attgtaaagt ttttgatac ctaatgtaag ttttctttgt gtaatattta      4920
tatgataaaa gacattagga tccctacaaa aaaaaaaaa aaaaaaaaa aaaaaaaaa         4980 aaaaaaaaaa aaaaaaaaaa aaaaaaaaaa aaaaaaaa a                            5021

<210> SEQ ID NO 4
<211> LENGTH: 9120
<212> TYPE: DNA
<213> ORGANISM: Homo Sapiens

<400> SEQUENCE: 4
gcggccgccg ccctcgccac cccgcctgcc cactcccgcc gccgcccgc tctcgctttc        60 cccccggcct ccctcgccc cttcccctcc cccttccgg cgcactcggg gggctgggaa        120
cgagctgcca tgtgatgcgc gtcccctccg cgagctttcg gtgacccacg aactgcccac       180
ctcgccggct gccgggaggg ggctgcgagc cgggaagacg cggggaagag gaggcggaaa       240
aggacgcaaa gttctccggc gagcgcattc attcacatag ctcccagttt taacatttcg       300
ccacctactg aagacatcat ttgggaccaa gctgatgagc cttgaagca cagcagataa        360 gagtgttgct gttgatcatc tttgcctggg aagttgaatg ataaagccag aagaaagcat      420
gctttctgat catttgcagc tgtctgcttc agaaagtgag ggctccagga atgaggagaa      480
tcttcaagaa cttcctcgca ctgtgacatg tctgatccct gctcccatc cctgcagcat      540 gaacaaggtg gacactcact gacctgtcac aaggttgccc cacaaaactt ggggtccat      600 gtctgaatgg attgccagag ccttctcatc tctcccttcg cccagttccc tgcatcctaa      660
gactcgaagg cagcacagga cctggaaaaa ttacatggtg tgaacggcat gtctgtggat      720
gagaagcctg actccccat gtatgtgtat gagtccacag tccactgcac caacatcctc      780
ctgggcctca atgaccagcg gaaaaggat attctctgtg acgtgacttt gatcgtggag      840
aggaaggagt tccgggccca ccggctgtg ctggccgcat gcagtgaata ttttttggcag      900 gcgctggttg gacagacaaa aaatgatttg gtggtcagct tgcctgagga ggtcacagcc      960
aggggctttg ggccgctgtt acagtttgcc tacactgcca agctgttact cagcagagaa     1020
aacatccgcg aggtcatccg ctgtgctgag ttcctgcgca tgcacaacct ggaggactcc     1080
tgcttcagct tcctgcagac ccagctcctg aacagtgagg atggcctgtt tgtgtgccgg     1140
aaggatgctg cgtgccagcg cccacacgag gactgcgaga actctgcagg agaggaggag     1200
gatgaagagg aggagacgat ggattcagag acggccaaga tggcttgccc cagggaccag     1260
atgcttccag agcccatcag ctttgaggcc gccgccatcc ccgtagcaga gaggaagaa      1320
```

```
gccctgctgc ccgagcctga cgtgcccaca gacaccaagg agagctcaga aaaggacgcg   1380
ttaacgcagt accccagata caagaaatac cagcttgcat gtaccaagaa tgtctataat   1440
gcatcatcac acagtacctc aggttttgca agcacattcc gggaagataa ctctagcaac   1500
agcctcaagc cggggcttgc caggggcag  attaaaagtg agccgcccag tgaagagaat   1560
gaggaagaga gcatcacgct ctgcctgtct ggagatgagc ctgacgccaa ggacagagcg   1620
ggggatgtcg agatggaccg gaaacagccc agccctgccc ctaccccac  ggccccagct   1680 ggggccgcct gcctggagag atccaggagc gtggcctcgc cctcctgctt aaggtctctg   1740
ttcagcataa cgaaaagtgt ggagctgtct ggcctgccca gtacatctca gcagcacttt   1800
gccaggagtc cagcctgccc ttttgacaag gggatcactc agggtgacct taaaactgac   1860 tacaccccatt tcacagggaa ttatggacag ccccacgtgg ccagaagga  ggtgtccaac   1920 ttcaccatgg ggtcgcccct caggggccct gggttggagg ctctctgtaa acaggaggga   1980
gagctggacc ggaggagcgt gatcttctcc tccagcgctt gtgaccaagt gagcacctcg   2040
gtgcattctt attctggggt gagcagtttg acaaagacc  tctctgagcc ggtgccaaag   2100
ggtctgtggg tgggagccgg ccagtccctc cccagctcgc aggcctactc ccacggtggg   2160
ctgatggccg accacttgcc aggaaggatg cggcccaaca ccagctgccc ggtgccaatc   2220
aaagtctgcc ctcgctcacc ccccttggag accaggacca ggacttccag ctcctgctct   2280
tcctattcct acgcggagga cgggagcggg ggctcaccct gcagcctccc tctctgtgag   2340
ttctcctcct cgccctgttc cagggagcc  agattccttg ccacagaaca tcaggaacca   2400
ggcctgatgg gagatggaat gtacaaccaa gtgcggcccc aaattaaatg tgagcagtct   2460
tatggaacca actccagtga cgaatccgga tcgttctcgg aagcagacag tgagtcgtgt   2520 cctgtgcagga caggggcca  ggaggtaaaa cttccttttc ctgtagatca aatcacagat   2580
cttccaagga acgatttcca tgatgatgatt aaaatgcaca agctaacctc agaacagtta   2640
gagtttattc atgatgtccg acggcgcagc aagaaccgca tcgcggccca cgctgccgc    2700 aaaaggaaac tggactgtat tcagaattta gaatgtgaaa tccgcaaatt ggtgtgtgag   2760
aaagagaaac tgttgtcaga gaggaatcaa ctgaaagcat gcatggggga actgttggac   2820
aacttctcct gccttttccca ggaagtttgc cgagacatcc agagcccga  gcagatccag   2880 gccctgcatc ggtattgccc tgtcctcaga cccatggact tgcccacggc ctccagtatt   2940
aaccctgcgc ccttgggtgc tgagcagaac attgcggcct cccaatgcgc agtgggggaa   3000
aacgtgccct gctgcttgga gccaggcgcg gctcccccccg accccccctg ggcacccagc   3060
aacacctccg agaattgtac ctctgggagg agactagaag gcactgaccc gggaaccttc   3120
tcagagagag gacctcctct tgaacccagg agccaaacag tgaccgtgga cttctgccag   3180
gaaatgactg ataagtgtac aactgacgaa cagcccagga agattatac  ctagtgactc   3240 ggctctgcct cccagtccgc acacctctcc catccaggcg ttcttcagtc agcctgtggc   3300
actgttcatc tgctgtcccg aagaaaccga gaacacattt ggtgcacact acagcggtct   3360
tagcagcaat actgttccga agtatcctct cctcttctcg agcaggagtg atagttacct   3420
tcacaatggt gctacccctt gcccaggcaa ggaaagacag cagtgatgac actgtctgtc   3480
tgtggctcaa tttcagtctt cacagggata gactacaaca cctctaggcc ccaaccacgg   3540
attttttttc tcagtggccc atgtcacaaa ccctatctca ggaatttctt ctgaatgttc   3600 aattttttc  attgaagaca gcttctatac acatcaaagt tttatagcta gactgtacat   3660
attatatata atatatatat aaaaaatata tatatatata tatatccata tgcaaaagtc   3720
```

```
ctgcatgcct caactttctc atcctaaaac tggaaactta tttctcattt agaaacaggt   3780
tccaacattc ctcttctttt gtctctgatg ctagaactag tttggtaact gttaacgtgg   3840 tcattttct  tgcttcacag ttcaattttc aattcgtact tatttatgga caaaattcag   3900
tgttggaagc ttttccccaa ggttttattt cagatttctt tttcgtttgg tttggttttg   3960
gcacctccaa gtggtgtcat ttgagcattg taggtttgtt ttttgtttgt ttgggggtt   4020 ttgtttgttt ttgtttttgt ttttgttttc cttgcagata ctgtacagta atggtcaact   4080
ttgccacttg cactgagttt tgggtcaaac ctattttctt aaatgaagtt gtaacttcgg   4140
tataactcaa gtatactgta tattctttgc ttttagttaa aaaagtaaaa cattttagct   4200
aattaaaaag cactcaggtg ataattatgt aggaaaaaca atcttgccaa ataatgaatt   4260
catcctagga tgtgtagaca ataatctgct tgaatatttt tatatttcac ctcctcccca   4320
cctttcccta agcaaagttt aaacgcagat agagagttca gagttgatgc tggatgttca   4380
gattcctaag tggggagaga gtttggacat ctcactcaaa agtacatcag aaaaacagga   4440
atccgtgatt ttataccaga actcagcagg cattggctcc tagaaatcaa gttagaaagt   4500
tttcacccag ggagtaagtc ccattcattt caacacgtcc tgaggcctcg gcttgctctt   4560
ggaagtggtg tgcagtagga cctgctcccc tgaaggacgg ggccaaccag ccactggctt   4620
tcctgcccag gcttggcctc ccaggacatc tggcctgagg ggatttgaat cacagccccg   4680
aaggtcctgc cttcacccca ttgggagaga gcagggcatc ctggcatctg cgatccatcc   4740
ctgcacaggc tgacacatt  ctttctcctt tccttctcca aaggcttgga gttttcttct   4800 gaggttttc  tgccagtgtc ttgtctgaag gcagacttca ttctgaggct ttggacaagc   4860
tattcaccgg gaaccctccc tgtccccttc ccgaatcaca cacatacctt accctcacct   4920
gatgataatt ttctcttctt gctgcaaaac tggttggctt gcaacccaga gagagcagct   4980
tcccttggct ctgggggccg tgttggcccc agccacgttt acaggaaggt gtgcccagag   5040
ggaggaggaa tcagctccct cgctccagtg gccttgggtc cgggtctcac tgagcagccc   5100
gagggccact ccagcccggc tggggaagag agtcctgaac ggtttgatgt ggggatgggg   5160
tggtgggcag tggggaatag atggttgact ttgtttcttt atttgtgcca ttgtttggac   5220
aatattaaag ctgcatgtaa aagggaaat  tagtatatga tgtaggctaa aagtgaaatc   5280
atagtaacat atgttttagt attattaact tttttctgta caaatattag cactaaatgt   5340
ttaaatatgt atgaatgcca gaaatttgtc agttcatgca gtaggataaa aaaaaaaaa   5400 aaaaaaaag  ggcttttctt tttaaacagt tccacttta  aaacctgcct ctgggttttt   5460 gtttttctt  gtttgtgtgt gtgtgtgtgt gtgtgtgtgt gtgtgtgtgt gtgtgtgtgt   5520
gtctgaaaca gatcttgata aagctctgtg ttggagctgc tggttttgt  tatggttgtt   5580 ggaatttctt ggcctactag gacagttctg tgcttcacca tgaggtttgc ctttgtggaa   5640
aactcgtggg tgacagtgag aatataaact caatgtgaat cacgtgatac ttcggcaggc   5700
gtgtgttaca gtggagtcag ctgacagtat tttgcttttt aactctattg ttgcctttcc   5760
aagtgacctc tcctcttctt ttaaaaaaag aacactttct gctcatatca taaccaggtc   5820
caacccagct tcttggcatg aggtttaccc tggtaacaac tcatgtgcaa ctggtagtct   5880
tgaccacatt ccatccattt cctcaggttt ctgtggttca gtagcccaga cctgtttggc   5940
agccatttct agcaggggcg gggcctcttt atttctctcc accctaactc agacctcacc   6000
ttcctcccac ccaccctgc  cttgctttc  ttcctcttcc cccaacctaa cttctgccat   6060
```

```
gggaactggt taaaaacact gctctaaaaa ccatcttcca atttcataga gatttctcac    6120
aagttatttc attcataatc caccatgaac agtgactagc ttcgtgcagt tgttcatgtg    6180
atgtgtgtgt gtcttttcct attcagaact atgtgcttgt caaaattatt tctgggttga    6240
ttcaaaggga ggacttgctg gggaccagaa tccaacggc ctcaagtgga attttaaaac    6300
ctagcctgtc tcttttccct gggatccctc tgtcaacccc acgccttta ggaaaaagaa    6360 aagtgagtga acagcaagga agagtgtttg cacagtacag taacatttgg ttgttcttaa    6420
ggctcttttc ttacaaaaat aagagaccct ccaaccacgg gctgtttagg aggatgcctg    6480
cttgggtctc caaatggctg gggtaggaat ggttgttggg gcagagccag tggaggtgag    6540
tgaccctgag actaatgaac atcccaccta aatccagtcc tccccttgga tctgcctttg    6600
tcctgcttgt gtatccaggc aacctctttt caagttggtc aggctttgga caggtgagtg    6660
atttgctgta tgtgtttgtt tctctgcgtt acctggggt gccttgatta aaatcgaact    6720
ttattacata ctgattctgg aacaaaacag ttagaaaaac tttaaacttt aaaaaaaaaa    6780
aaaccgacaa agttacgagg ccatcctgct atttatcttc tgagttccca gcaatgactc    6840
aggcatcaga gatgatgctg cagtggaaaa cctgactctg tgtgtctgca actgaatgtt    6900
gtgcgagtaa tttattaact gtcttttctaa aggtttgctg cttttaagat gcactataat    6960
tcgggatgta atccttacat tgcttttcca aggaagggaa caaaagtcta gtgattagta    7020
tgccaactgc cactactcct tcaaaaggag ccaggaccag cgacaagact catgagagga    7080
ctggctaaag tgaagtgtgc acagtgtgaa gtttaatgct gttgtcaaga ggcctaaacc    7140
cacattttct cttttaatat tttatgattg ccatcaaaga agaagaaaaa gaaggaacag    7200
acaaaggttt gaaaatgata agcctgttaa gacaccaaaa actcctgtcc cgtgaagctg    7260
cttgacatcc tgtggagtag cataatcctc tcaaatgag gaagagctgc ctgcaaagct    7320
ttctcaagtc cctatttggc tacctacttc tctacattat gccccattta aactaggagc    7380
tgtcttagaa atgacttcaa actgcttcac tattgcttac agtttaggag gagtctcaga    7440
tccagaagga gcaagaatca gtttggtcc tcaaatgact gtaaatagac taaagaacaa    7500 ggtgttttt gttttgttt tgttttcta agaataaagc tgttcgttgt atcatgagtt    7560
agtgtttctt ccccaaactg aagactgtgt tggaagtgca atttctggtg agtcagtcca    7620
caatacaatg ccctgtgtgg agttggtatt catacaggaa atctgtgtgc acgaggcatt    7680
gtgtgttgaa agtgtatgtt tatagtactg cctgagccat ctcatgaccc cagcgtccaa    7740
aaccgatgct gtagaacaga acatatctgt cacaaatagg tgtgtgcaaa tagcatttgt    7800
acatagaaaa gtctcattgt ggcagattga gcataaatta ttcaactgac ggtgcaaaaa    7860
cattacttgc aaagaaaagt ttatagtatt ttcctacact ccaccctggg agatgatatt    7920
tctatcaaat gaatatcagt gcattttaaa tgtaatatga aaacgatgct gccattttgt    7980
gaagaatacc cacttggttg cagaggccaa ctttcatagc tttgatttaa tgttgtgaca    8040
cggtgtatgc attttgctgt caagcaatgg ataaacagct ctgactttca ttctcattcc    8100
agtttattga cctcagataa aacactggcc cttcttagaa gcagaagtgt gcaccaagac    8160
cattcatttc aggtagactc acattcagtg ccaagtgctc ccatgggaat aatcagacgc    8220
atatgttgcg aaagagtgaa gggacttgga caaagagggg ttttcctaca gatggatgct    8280
cagtcttcta ccaaaacatg tttggaggca gaactatgac ctccccttaa gtcctaacaa    8340 tgtatttgt gtgtgcaaat cctgggatgc ccgtttcacg ctctgacata aagacatggc    8400
acctctagtg agtgatcagg aagattccat atgcatttgg gagcttcagg tgcttgttag    8460
```

| | |
|---|---|
| acacagtgag ccattcaagg caagcaccac ctttgctagt gaggccaaga gagcctgtga | 8520 |
| caatttgaca atttgttcca gaaccagtct gatgcaagtg cacctctaat atatgcctta | 8580 |
| caaactccag aggccatatt caaaacaggg tcttctcagt gtatgcaagg ggctgcagcc | 8640 |
| cctcttctct tcctcccag gttgaacaat acggacagtt tcacacata tctacctgta | 8700 |
| taaccctctg tacctctcat aactggtcaa cgactgtaac aggttacatc aggtgttttt | 8760 |
| ctacatactt tttacacaga ttctatgcga ttaatgtaat ttaattcaat gcatcatttt | 8820 |
| attgtactag ttcttaggct tgtccttatt ttttctaag tgattgtggt ttttctcgtg | 8880 |
| gttttattg taaaaatga aaggctgttg atgcttattc tctgtaacta agaattttac | 8940 |
| cttttggggg aaaaaagcat tgctatgaac taatggaatt ggaacttcat ttactcattg | 9000 |
| taaatacact attgtgcaaa aaagttttc actcaattga attgctagtg ttaactgaat | 9060 |
| tttgtctaga caccatttct gttgatgaaa taaagacata tcattatgca ttgtaaactg | 9120 |

<210> SEQ ID NO 5
<211> LENGTH: 1062
<212> TYPE: DNA
<213> ORGANISM: Homo Sapiens

<400> SEQUENCE: 5

| | |
|---|---|
| atgaatgagt gtcactatga caagcacatg gactttttt ataataggag caacactgat | 60 |
| actgtcgatg actggacagg aacaaagctt gtgattgttt tgtgtgttgg gacgttttc | 120 |
| tgcctgttta ttttttttc taattctctg gtcatcgcgg cagtgatcaa aaacagaaaa | 180 |
| tttcatttcc ccttctacta cctgttggct aatttagctg ctgccgattt cttcgctgga | 240 |
| attgcctatg tattcctgat gtttaacaca ggcccagttt caaaaacttt gactgtcaac | 300 |
| cgctggtttc tccgtcaggg gcttctggac agtagcttga ctgcttccct caccaacttg | 360 |
| ctggttatcg ccgtggagag gcacatgtca atcatgagga tgcgggtcca tagcaacctg | 420 |
| accaaaaaga gggtgacact gctcattttg cttgtctggg ccatcgccat ttttatgggg | 480 |
| gcggtcccca cactgggctg gaattgcctc tgcaacatct ctgcctgctc ttccctggcc | 540 |
| cccatttaca gcaggagtta ccttgttttc tggacagtgt ccaacctcat ggccttcctc | 600 |
| atcatggttg tggtgtacct gcggatctac gtgtacgtca agaggaaaac caacgtcttg | 660 |
| tctccgcata caagtgggtc catcagccgc cggaggacac ccatgaagct aatgaagacg | 720 |
| gtgatgactg tcttagggc gtttgtggta tgctggaccc cgggcctggt ggttctgctc | 780 |
| ctcgacggcc tgaactgcag gcagtgtggc gtgcagcatg tgaaaggtg gttcctgctg | 840 |
| ctggcgctgc tcaactccgt cgtgaacccc atcatctact cctacaagga cgaggacatg | 900 |
| tatggcacca tgaagaagat gatctgctgc ttctctcagg agaacccaga gaggcgtccc | 960 |
| tctcgcatcc cctccacagt cctcagcagg agtgacacag gcagccagta catagaggat | 1020 |
| agtattagcc aaggtgcagt ctgcaataaa agcacttcct aa | 1062 |

<210> SEQ ID NO 6
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 6

| | |
|---|---|
| gcatttaact ggaggaactt t | 21 |

```
<210> SEQ ID NO 7
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 7
caagagttct ggagagagat t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 8
gaacagagct catgaggtct t                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 9
aatcaagata cgagtggaat t                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 10
ggatcgagcc agtgagtctt t                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 11
cggcgagcat ggtgcaaatt t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 12
ggaactggat ctcaggcaat t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic Sequence
```

```
<400> SEQUENCE: 13
gtggatgagc tgacgctaat t                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 14
gaaaatggga gttggtgaat t                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 15
acgccaaggt ctccaacaat t                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 16
ggacatggcc ctaacctgat t                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 17
gggagagagt ggatcagatt t                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 18
ccaaactcat cctggaagat t                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 19
gagtctgaca cgtgggtgat t                                              21

<210> SEQ ID NO 20
```

<211> LENGTH: 21
<212> TYPE: DNA
<213> ORGANISM: Artificial Sequence
<220> FEATURE:
<223> OTHER INFORMATION: Synthetic Sequence

<400> SEQUENCE: 20
ggagagagag caagcgccat t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 21
gaagagagct ggagacaggt t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 22
gggaattcgc catgaccttt t                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 23
ggccctaacc tgaggctgat t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 24
cgtgaagcct tgcaccaaat t                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 25
ggaaaatggg agttggtgat t                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 26
gggcgaacgc agcatttaat t					21

<210> SEQ ID NO 27
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 27
agttctggag agagagcaat t					21

<210> SEQ ID NO 28
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 28
gtgaagacca gaaggtggat t					21

<210> SEQ ID NO 29
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 29
aggctgagca atttaactat t					21

<210> SEQ ID NO 30
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 30
cagcagatgc agcggggaat t					21

<210> SEQ ID NO 31
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 31
ggacagtggt atcagaatct t					21

<210> SEQ ID NO 32
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 32
agacgcagct ctacgccaat t					21

<210> SEQ ID NO 33
<211> LENGTH: 21
<212> TYPE: DNA

<213> ORGANISM: Artificial Sequence
<220> FEATURE:
<223> OTHER INFORMATION: Synthetic Sequence

<400> SEQUENCE: 33
aggcatggct gcagcaatgt t                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 34
tggaagaact caaactggat t                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 35
ctgaagagag ctggagacat t                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 36
aacctgaggc tgagcaattt t                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 37
gcaccaaaca gctgcatctt t                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 38
gcactctact cccgagacat t                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 39
gggtgaagca caggatgtat t                                              21

<210> SEQ ID NO 40
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 40
ccacaaacgg caaggagtct t                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 41
caaacggcaa ggagtcttat t                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 42
ggtgaagcca gcagcagatt t                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 43
caaaatggga agctggcaat t                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 44
gcctggaaga gctgaaagat t                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 45
aagagctgaa agaggcaaat t                                              21

<210> SEQ ID NO 46
<211> LENGTH: 21
<212> TYPE: DNA
<213> ORGANISM: Artificial Sequence
<220> FEATURE:

<223> OTHER INFORMATION: Synthetic Sequence

<400> SEQUENCE: 46
cggtgaagac cctgacccat t                                                  21

<210> SEQ ID NO 47
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 47
gagccctatt ccagtacaat t                                                  21

<210> SEQ ID NO 48
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 48
gcaaggagtc ttagcagctt t                                                  21

<210> SEQ ID NO 49
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 49
ccattatcat cgtgtggcat t                                                  21

<210> SEQ ID NO 50
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 50
ggaagagctg aaagaggcat t                                                  21

<210> SEQ ID NO 51
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 51
caacattgac actgattact t                                                  21

<210> SEQ ID NO 52
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 52
gaaaataaag aggaaggaat t                                                  21

<210> SEQ ID NO 53
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 53
cttcaagagt tctggagagt t                                            21

<210> SEQ ID NO 54
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 54
ccggaaaact acacggatct t                                            21

<210> SEQ ID NO 55
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 55
gtgaagcaca ggatgtacat t                                            21

<210> SEQ ID NO 56
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 56
gcacagagct ccatccagat t                                            21

<210> SEQ ID NO 57
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 57
gctataaact gctgatccat t                                            21

<210> SEQ ID NO 58
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 58
tcacatactt taaagccaat t                                            21

<210> SEQ ID NO 59
<211> LENGTH: 21
<212> TYPE: DNA
<213> ORGANISM: Artificial Sequence
<220> FEATURE:
<223> OTHER INFORMATION: Synthetic Sequence

```
<400> SEQUENCE: 59
gggcagcacc gtagacctat t                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 60
ggtcagtggt catcacattt t                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 61
acgcaggagc tgagaggttt t                                              21

<210> SEQ ID NO 62
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 62
cctatcagcc agaaacaaat t                                              21

<210> SEQ ID NO 63
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 63
tcagaatggc cttgatctat t                                              21

<210> SEQ ID NO 64
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 64
ggaaaaggca gctgcaacat t                                              21

<210> SEQ ID NO 65
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 65
gggcaatgaa tgcagccaat t                                              21

<210> SEQ ID NO 66
<211> LENGTH: 21
```

```
<212> TYPE: DNA
<213> ORGANISM: Artificial Sequence
<220> FEATURE:
<223> OTHER INFORMATION: Synthetic Sequence

<400> SEQUENCE: 66
aggagtggtc ccagggctat t                                              21

<210> SEQ ID NO 67
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 67
ccgaacgcct ggaggagttt t                                              21

<210> SEQ ID NO 68
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 68
gagcaacaag caaggaaaat t                                              21

<210> SEQ ID NO 69
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 69
ggagacaaat gctcaccaat t                                              21

<210> SEQ ID NO 70
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 70
ccagatcagt cctagcttat t                                              21

<210> SEQ ID NO 71
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 71
gaatatacct ccttcagatt t                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 72
```
gtttgaaggt tgcgagaagt t                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 73
ggacgcatct ggacaccaat t                                              21

<210> SEQ ID NO 74
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 74
agagcaacaa gcaaggaaat t                                              21

<210> SEQ ID NO 75
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 75
agccaaagca gcaggagttt t                                              21

<210> SEQ ID NO 76
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 76
gctttgggcc tcagtgcaat t                                              21

<210> SEQ ID NO 77
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 77
tattcaagcc gaagtggaat t                                              21

<210> SEQ ID NO 78
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 78
cttcaatact gcaaagaact t                                              21

<210> SEQ ID NO 79
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 79
ctaacaacct ccatctcaat t          21

<210> SEQ ID NO 80
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 80
gcaacaatct agtggtcact t          21

<210> SEQ ID NO 81
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 81
cctcaagcat gaagcaggat t          21

<210> SEQ ID NO 82
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 82
ggatggctcc tcagaacaat t          21

<210> SEQ ID NO 83
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 83
accttgagtc tgacggaaat t          21

<210> SEQ ID NO 84
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 84
gtaccaaacg ctacacagat t          21

<210> SEQ ID NO 85
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 85
ctgtctacac cgaaggctat t          21

```
<210> SEQ ID NO 86
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 86
tgtctacacc gaaggctaat t                                              21

<210> SEQ ID NO 87
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 87
gcatgaagca ggagtggtct t                                              21

<210> SEQ ID NO 88
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 88
ccaaagagca acaagcaagt t                                              21

<210> SEQ ID NO 89
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 89
tagagatgct gctgctgaat t                                              21

<210> SEQ ID NO 90
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 90
agcaattatt caagccgaat t                                              21

<210> SEQ ID NO 91
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 91
tcagatacca ggtcccttat t                                              21

<210> SEQ ID NO 92
<211> LENGTH: 21
<212> TYPE: DNA
<213> ORGANISM: Artificial Sequence
<220> FEATURE:
<223> OTHER INFORMATION: Synthetic Sequence
```

```
<400> SEQUENCE: 92
cctagcttac agagggcaat t                                              21

<210> SEQ ID NO 93
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 93
ttgtcaaatt ccaggatgtt t                                              21

<210> SEQ ID NO 94
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 94
acccaagttc cctaagaaat t                                              21

<210> SEQ ID NO 95
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 95
cctaagaaag catgtgaagt t                                              21

<210> SEQ ID NO 96
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 96
tcctccaaat cctgggaaat t                                              21

<210> SEQ ID NO 97
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 97
ccttatttcg cgtgagtctt t                                              21

<210> SEQ ID NO 98
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 98
cagtcggcct caagcatgat t                                              21

<210> SEQ ID NO 99
```

```
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 99
acacaggcga gaagccgtat t                                              21

<210> SEQ ID NO 100
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 100
caccaaacct tatgcttgtt t                                              21

<210> SEQ ID NO 101
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 101
accttatgct tgtcaaattt t                                              21

<210> SEQ ID NO 102
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 102
cagcaattat tcaagccgat t                                              21

<210> SEQ ID NO 103
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 103
ccacagagcc ttctcgactt t                                              21

<210> SEQ ID NO 104
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 104
ccaatgggaa gccgcgattt t                                              21

<210> SEQ ID NO 105
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 105
```
ggaaaggggc tcttggcttt t                                              21

<210> SEQ ID NO 106
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 106
aagcaagact agaggcaaat t                                              21

<210> SEQ ID NO 107
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 107
gaaacttact caaaggatat t                                              21

<210> SEQ ID NO 108
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 108
ccagaaacta cgacaattat t                                              21

<210> SEQ ID NO 109
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 109
tgaaatatgc acagaagaat t                                              21

<210> SEQ ID NO 110
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 110
ccacagagct ccaccactat t                                              21

<210> SEQ ID NO 111
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 111
ggaaagtgaa cgtccataat t                                              21

<210> SEQ ID NO 112
<211> LENGTH: 21
<212> TYPE: DNA

```
<213> ORGANISM: Artificial Sequence
<220> FEATURE:
<223> OTHER INFORMATION: Synthetic Sequence

<400> SEQUENCE: 112
gcaaacacgt ccagaggatt t                                              21

<210> SEQ ID NO 113
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 113
ggatgaaatc tatgagcttt t                                              21

<210> SEQ ID NO 114
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 114
cctaaagatc caactgaaat t                                              21

<210> SEQ ID NO 115
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 115
acaaggatat cgatgtaaat t                                              21

<210> SEQ ID NO 116
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 116
ggatatcgtt ctctgattat t                                              21

<210> SEQ ID NO 117
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 117
aaacaaggat atcgatgtat t                                              21

<210> SEQ ID NO 118
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 118
tggttgtgtt tgagtgtaat t                                              21
```

<210> SEQ ID NO 119
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 119
tggtgaaagc taagggtgat t                                              21

<210> SEQ ID NO 120
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 120
gcaaagatct ggttgtgttt t                                              21

<210> SEQ ID NO 121
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 121
ttgtcaagtg ggagaataat t                                              21

<210> SEQ ID NO 122
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 122
gcacagaaga aaatagaatt t                                              21

<210> SEQ ID NO 123
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 123
tcaataaggt tctcggtgat t                                              21

<210> SEQ ID NO 124
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 124
cgaccaggat ggatacattt t                                              21

<210> SEQ ID NO 125
<211> LENGTH: 21
<212> TYPE: DNA
<213> ORGANISM: Artificial Sequence
<220> FEATURE:

<223> OTHER INFORMATION: Synthetic Sequence

<400> SEQUENCE: 125
cgggatgaac tgtcacaaat t                                              21

<210> SEQ ID NO 126
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 126
gcccagtctt ggtcagaaat t                                              21

<210> SEQ ID NO 127
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 127
aggaactggt gaaagctaat t                                              21

<210> SEQ ID NO 128
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 128
gctccatgca cctgaggaat t                                              21

<210> SEQ ID NO 129
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 129
gaataaagac tccctcatat t                                              21

<210> SEQ ID NO 130
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 130
aggtattgga taacagaatt t                                              21

<210> SEQ ID NO 131
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 131
aagctaaggg tgaggagttt t                                              21

<210> SEQ ID NO 132
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 132
acactgagga tgaaatctat t                                              21

<210> SEQ ID NO 133
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 133
tgacaactgt gctggatttt t                                              21

<210> SEQ ID NO 134
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 134
ggatatcgat gtaaagactt t                                              21

<210> SEQ ID NO 135
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 135
aataaagact ccctcataat t                                              21

<210> SEQ ID NO 136
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 136
gatggaaacc tgtgtcgaat t                                              21

<210> SEQ ID NO 137
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 137
gagagaggct ccgcggaaat t                                              21

<210> SEQ ID NO 138
<211> LENGTH: 21
<212> TYPE: DNA
<213> ORGANISM: Artificial Sequence
<220> FEATURE:
<223> OTHER INFORMATION: Synthetic Sequence

```
<400> SEQUENCE: 138
gggtacaact gatggttctt t                                              21

<210> SEQ ID NO 139
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 139
gggatgagat cacagcctat t                                              21

<210> SEQ ID NO 140
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 140
gtaagaagcg agccaagaat t                                              21

<210> SEQ ID NO 141
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 141
ataaagactc cctcataaat t                                              21

<210> SEQ ID NO 142
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 142
gaaatatgca cagaagaaat t                                              21

<210> SEQ ID NO 143
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 143
ggaaacctgt gtcgaagtat t                                              21

<210> SEQ ID NO 144
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 144
ggtattggat aacagaattt t                                              21

<210> SEQ ID NO 145
<211> LENGTH: 21
```

```
<212> TYPE: DNA
<213> ORGANISM: Artificial Sequence
<220> FEATURE:
<223> OTHER INFORMATION: Synthetic Sequence

<400> SEQUENCE: 145
agctaagggt gaggagttat t                                              21

<210> SEQ ID NO 146
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 146
tgacacaact caaatcaatt t                                              21

<210> SEQ ID NO 147
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 147
cagaagagct atccgagcat t                                              21

<210> SEQ ID NO 148
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 148
ccttctgtgt gatggacaat t                                              21

<210> SEQ ID NO 149
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 149
cctcacaact tccaagagat t                                              21

<210> SEQ ID NO 150
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 150
gagtgatcaa acaaggatat t                                              21

<210> SEQ ID NO 151
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 151
```
gatcaaacaa ggatatcgat t                                              21

<210> SEQ ID NO 152
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 152
aggaagacag cccaggatat t                                              21

<210> SEQ ID NO 153
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 153
ccaagaactg gaacaggaat t                                              21

<210> SEQ ID NO 154
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 154
aagaactgga acaggaaatt t                                              21

<210> SEQ ID NO 155
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 155
ccctaaagat ccaactgaat t                                              21

<210> SEQ ID NO 156
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 156
gaagataact ctagcaacat t                                              21

<210> SEQ ID NO 157
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 157
gtgaagagaa tgaggaagat t                                              21

<210> SEQ ID NO 158
<211> LENGTH: 21
<212> TYPE: DNA
<213> ORGANISM: Artificial Sequence

```
<220> FEATURE:
<223> OTHER INFORMATION: Synthetic Sequence

<400> SEQUENCE: 158
caaattggtg tgtgagaaat t                                              21

<210> SEQ ID NO 159
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 159
caggagagga ggaggatgat t                                              21

<210> SEQ ID NO 160
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 160
agaatgagga agagagcatt t                                              21

<210> SEQ ID NO 161
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 161
cagaacagtt agagtttatt t                                              21

<210> SEQ ID NO 162
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 162
ggaaatgact gataagtgtt t                                              21

<210> SEQ ID NO 163
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 163
ctttgatcgt ggagaggaat t                                              21

<210> SEQ ID NO 164
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 164
gagaggagga ggatgaagat t                                              21
```

<210> SEQ ID NO 165
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 165
gtaccaagaa tgtctataat t                                               21

<210> SEQ ID NO 166
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 166
gagatgagcc tgacgccaat t                                               21

<210> SEQ ID NO 167
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 167
gagaaactgt tgtcagagat t                                               21

<210> SEQ ID NO 168
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 168
agagaggaat caactgaaat t                                               21

<210> SEQ ID NO 169
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 169
cagtgaagag aatgaggaat t                                               21

<210> SEQ ID NO 170
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 170
ggtgtgtgag aaagagaaat t                                               21

<210> SEQ ID NO 171
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 171
gaggaggaga cgatggattt t                                              21

<210> SEQ ID NO 172
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 172
gggaagataa ctctagcaat t                                              21

<210> SEQ ID NO 173
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 173
aaaggaaact ggactgtatt t                                              21

<210> SEQ ID NO 174
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 174
gcaaattggt gtgtgagaat t                                              21

<210> SEQ ID NO 175
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 175
aagagaaact gttgtcagat t                                              21

<210> SEQ ID NO 176
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 176
atgaagagga ggagacgatt t                                              21

<210> SEQ ID NO 177
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 177
ggttggaggc tctctgtaat t                                              21

<210> SEQ ID NO 178

```
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 178
cagcaacacc tccgagaatt t                                              21

<210> SEQ ID NO 179
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 179
aaacagtgac cgtggacttt t                                              21

<210> SEQ ID NO 180
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 180
gaacagccca ggaaagattt t                                              21

<210> SEQ ID NO 181
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 181
cctcagaaca gttagagttt t                                              21

<210> SEQ ID NO 182
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 182
gtgctgagtt cctgcgcatt t                                              21

<210> SEQ ID NO 183
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 183
gcgagaactc tgcaggagat t                                              21

<210> SEQ ID NO 184
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 184
```
ctgcaggaga ggaggaggat t                                              21

<210> SEQ ID NO 185
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 185
ccgtagcaga gaaggaagat t                                              21

<210> SEQ ID NO 186
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 186
gccagaagga ggtgtccaat t                                              21

<210> SEQ ID NO 187
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 187
gggtgagcag tttggacaat t                                              21

<210> SEQ ID NO 188
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 188
ccaggaaaga ttatacctat t                                              21

<210> SEQ ID NO 189
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 189
cctcaatgac cagcggaaat t                                              21

<210> SEQ ID NO 190
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 190
ctgttactca gcagagaaat t                                              21

<210> SEQ ID NO 191
<211> LENGTH: 21
<212> TYPE: DNA

```
<213> ORGANISM: Artificial Sequence
<220> FEATURE:
<223> OTHER INFORMATION: Synthetic Sequence

<400> SEQUENCE: 191
gccaggaaat gactgataat t                                              21

<210> SEQ ID NO 192
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 192
agaaggaggt gtccaacttt t                                              21

<210> SEQ ID NO 193
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 193
ccaaattaaa tgtgagcagt t                                              21

<210> SEQ ID NO 194
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 194
aggaatcaac tgaaagcatt t                                              21

<210> SEQ ID NO 195
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 195
caggaagttt gccgagacat t                                              21

<210> SEQ ID NO 196
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 196
aggaggagga tgaagaggat t                                              21

<210> SEQ ID NO 197
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 197
aggaggatga agaggaggat t                                              21
```

<210> SEQ ID NO 198
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 198
accaaggaga gctcagaaat t                                              21

<210> SEQ ID NO 199
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 199
tcacagggaa ttatggacat t                                              21

<210> SEQ ID NO 200
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 200
gttggaggct ctctgtaaat t                                              21

<210> SEQ ID NO 201
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 201
gagaccagga ccaggacttt t                                              21

<210> SEQ ID NO 202
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 202
ccacagaaca tcaggaacct t                                              21

<210> SEQ ID NO 203
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 203
ttaaatgtga gcagtcttat t                                              21

<210> SEQ ID NO 204
<211> LENGTH: 21
<212> TYPE: DNA
<213> ORGANISM: Artificial Sequence
<220> FEATURE:

<223> OTHER INFORMATION: Synthetic Sequence

<400> SEQUENCE: 204
tctcggaagc agacagtgat t                                              21

<210> SEQ ID NO 205
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 205
cttgaaccca ggagccaaat t                                              21

<210> SEQ ID NO 206
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 206
cctacaagga cgaggacatt t                                              21

<210> SEQ ID NO 207
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 207
tctactacct gttggctaat t                                              21

<210> SEQ ID NO 208
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 208
tcatcatggt tgtggtgtat t                                              21

<210> SEQ ID NO 209
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 209
gtacatagag gatagtattt t                                              21

<210> SEQ ID NO 210
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 210
gtcgatgact ggacaggaat t                                              21

<210> SEQ ID NO 211
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 211
gtggagaggc acatgtcaat t                                              21

<210> SEQ ID NO 212
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 212
ggatgcgggt ccatagcaat t                                              21

<210> SEQ ID NO 213
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 213
ccatgaagct aatgaagact t                                              21

<210> SEQ ID NO 214
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 214
aataggagca acactgatat t                                              21

<210> SEQ ID NO 215
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 215
agtacataga ggatagtatt t                                              21

<210> SEQ ID NO 216
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 216
caataaaagc acttcctaat t                                              21

<210> SEQ ID NO 217
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 217
atgacaagca catggacttt t					21

<210> SEQ ID NO 218
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 218
gtgtacgtca agaggaaaat t					21

<210> SEQ ID NO 219
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 219
aagctaatga agacggtgat t					21

<210> SEQ ID NO 220
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 220
gcaccatgaa gaagatgatt t					21

<210> SEQ ID NO 221
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 221
agaggatagt attagccaat t					21

<210> SEQ ID NO 222
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 222
ccgatttctt cgctggaatt t					21

<210> SEQ ID NO 223
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 223
acacaggccc agtttcaaat t					21

<210> SEQ ID NO 224
<211> LENGTH: 21

```
<212> TYPE: DNA
<213> ORGANISM: Artificial Sequence
<220> FEATURE:
<223> OTHER INFORMATION: Synthetic Sequence

<400> SEQUENCE: 224
ccatttacag caggagttat t                                              21

<210> SEQ ID NO 225
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 225
ggacacccat gaagctaatt t                                              21

<210> SEQ ID NO 226
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 226
acaaggacga ggacatgtat t                                              21

<210> SEQ ID NO 227
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 227
tgtccaacct catggccttt t                                              21

<210> SEQ ID NO 228
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 228
cctcagcagg agtgacacat t                                              21

<210> SEQ ID NO 229
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 229
gccagtacat agaggatagt t                                              21

<210> SEQ ID NO 230
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 230
```
taatttagct gctgccgatt t        21

<210> SEQ ID NO 231
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 231
cctatgtatt cctgatgttt t        21

<210> SEQ ID NO 232
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 232
taacacaggc ccagtttcat t        21

<210> SEQ ID NO 233
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 233
cccatgaagc taatgaagat t        21

<210> SEQ ID NO 234
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 234
cagccagtac atagaggatt t        21

<210> SEQ ID NO 235
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 235
gaggatagta ttagccaagt t        21

<210> SEQ ID NO 236
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 236
ctggaattgc ctatgtattt t        21

<210> SEQ ID NO 237
<211> LENGTH: 21
<212> TYPE: DNA
<213> ORGANISM: Artificial Sequence

```
<220> FEATURE:
<223> OTHER INFORMATION: Synthetic Sequence

<400> SEQUENCE: 237
tggagaggca catgtcaatt t                                              21

<210> SEQ ID NO 238
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 238
catagcaacc tgaccaaaat t                                              21

<210> SEQ ID NO 239
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 239
aggacaccca tgaagctaat t                                              21

<210> SEQ ID NO 240
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 240
tggcgtgcag catgtgaaat t                                              21

<210> SEQ ID NO 241
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 241
acactgatac tgtcgatgat t                                              21

<210> SEQ ID NO 242
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 242
ggatagtatt agccaaggtt t                                              21

<210> SEQ ID NO 243
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 243
cgatttcttc gctggaattt t                                              21
```

<210> SEQ ID NO 244
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 244
cgatgactgg acaggaacat t                                              21

<210> SEQ ID NO 245
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 245
catacaagtg ggtccatcat t                                              21

<210> SEQ ID NO 246
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 246
tagtattagc caaggtgcat t                                              21

<210> SEQ ID NO 247
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 247
tcatcgcggc agtgatcaat t                                              21

<210> SEQ ID NO 248
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 248
tgaagacggt gatgactgtt t                                              21

<210> SEQ ID NO 249
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 249
ctggacagga acaaagcttt t                                              21

<210> SEQ ID NO 250
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 250
ggtcatcgcg gcagtgatct t                                                21

<210> SEQ ID NO 251
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 251
ggagcaacac tgatactgtt t                                                21

<210> SEQ ID NO 252
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 252
cttctggaca gtagcttgat t                                                21

<210> SEQ ID NO 253
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 253
gagaggcaca tgtcaatcat t                                                21

<210> SEQ ID NO 254
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 254
tgacaagcac atggactttt t                                                21

<210> SEQ ID NO 255
<211> LENGTH: 21
<212> TYPE: DNA

```
<213> ORGANISM: Artificial Sequence
<220> FEATURE:
<223> OTHER INFORMATION: Synthetic Sequence

<400> SEQUENCE: 255
cccatttaca gcaggagttt t                                              21
```

GENETIC ALTERATIONS ON CHROMOSOMES 21Q, 6Q AND 15Q AND METHODS OF USE THEREOF FOR THE DIAGNOSIS AND TREATMENT OF TYPE 1 DIABETES

This application is a continuation of U.S. application Ser. No. 12/947,564 filed Nov. 16, 2010, which is a § 365 application of PCT/US2009/044356 filed May 18, 2009, which claims priority to U.S. Provisional Application 61/054,040 filed May 16, 2008, each of the aforementioned applications being incorporated herein by reference.

FIELD OF THE INVENTION

This invention relates to the fields of glucose metabolism, genetics and pathology associated with diabetes, particularly type I diabetes. More specifically, the invention provides a panel of genes containing genetic alterations, e.g., single nucleotide polymorphisms, which had heretofore not been associated with this disease. Methods and kits for using the sequences so identified for diagnostic and therapeutic treatment purposes are also provided, as are therapeutic compositions for management of diabetes.

BACKGROUND OF THE INVENTION

Several publications and patent documents are cited throughout the specification in order to describe the state of the art to which this invention pertains. Each of these citations is incorporated herein by reference as though set forth in full.

Type I diabetes (T1D) results from the autoimmune destruction of pancreatic beta cells, a process believed to be strongly influenced by multiple genes and environmental factors. The incidence of T1D has been increasing in Western countries and has more than doubled in the United States over the past 30 years. The disease shows a strong familial component, with first-degree relatives of cases being at 15 times greater risk of T1D than a randomly selected member of the general population and monozygotic twins being concordant for T1D at a frequency of approximately 50%. However, while the genetic evidence is strong, the latter data suggests that an interplay with environmental factors also plays a key role in influencing T1D outcome.

The familial clustering of T1D is influenced by multiple genes. Variation in four loci has already been established to account for a significant proportion of the familial aggregation of T1D. These include the major histocompatibility complex (MHC) region on 6p21 (including the HLA-DRB1, -DQA1 and -DRQ1 genes[1]); the insulin/insulin-like growth factor 2 gene complex (INS-IGF2) on 11p15[2-4], the protein tyrosine phosphatase-22 (PTPN22) gene on 1p13[5,6] and the gene encoding cytotoxic T-lymphocyte-associated protein 4 (CTLA4) on 2q31[7,8]. The interleukin-2 receptor alpha (CD25) locus on 10p15[9] has also been implicated in the pathogenesis of T1D but remains to be replicated by independent studies. In addition, spontaneous mouse model studies of T1D have implicated numerous other regions that have been confirmed in replication studies[10]. Several other loci have also been implicated in human association studies with T1D but the effects of these implicated genes remain controversial and are subject to confirmation in independent studies utilizing sufficient sample sizes. Together, these studies suggest that many more T1D susceptibility genes remain to be discovered.

SUMMARY OF THE INVENTION

In accordance with the present invention, T1D-associated SNPs have been identified which are indicative of an increased or reduced risk of developing T1D. Thus, in one aspect, nucleic acids comprising at least one genetic alteration identified in Tables 1, 2, 4 and 5 are provided. Such nucleic acids and the proteins encoded thereby have utility in the diagnosis and management of type 1 diabetes (T1D).

In another aspect of the invention, methods for assessing susceptibility for developing T1D are provided. An exemplary method entails providing a target nucleic acid from a patient sample, said target nucleic acid having a predetermined sequence in the normal population, and assessing said target nucleic acid for the presence of at least one genetic alteration, e.g., a single nucleotide polymorphism, which is indicative of an increased or decreased risk of developing T1D. Such genetic alterations include, without limitation, inversion, deletion, duplication, and insertion of at least one nucleotide in said sequence.

Preferably, the genetic alteration is a single nucleotide polymorphism present in UBASH3A, GLIS3, RASGRP1, BACH2, and EDG7 encoding nucleic acids and genetic regions associated therewith. Such genetic regions include the linkage disequilibrium blocks provided in Table 3 and the method entails detecting any variant associated with diabetes in such blocks. Preferably, the SNP is rs9976767 present on chromosome 21 at position 42709459 within the UBASH3A gene, the SNP is rs3757247 present on chromosome 6 at position 91014184 in the BACH2 gene or the SNP is rs7171171 at position 36694333 on chromosome 15 in the RASGRP1 gene.

The methods of the invention also include the detection of any of the T1D associated genetic alterations comprising the single nucleotide polymorphisms set forth in Tables 1, 2, 4 or 5 for the diagnosis of T1D. Alternatively or in addition, genetic alterations associated with T1D present in the linkage disequilibrium blocks set forth in Table 3 can be detected. Kits and microarrays for practicing the foregoing methods are also provided.

In yet another embodiment, a method of managing T1D is provided which entails administering a therapeutic agent to a patient in need thereof. The therapeutic agent can be a small molecule, an antibody, a protein, an oligonucleotide, or a siRNA molecule.

In another aspect of the invention, a method for identifying agents that bind and/or modulate UBASH3A, GLIS3, RASGRP1, BACH2, and EDG7 functional activity is provided, as well as pharmaceutical compositions comprising said agent in a biologically acceptable carrier.

DETAILED DESCRIPTION OF THE INVENTION

Figure 1:
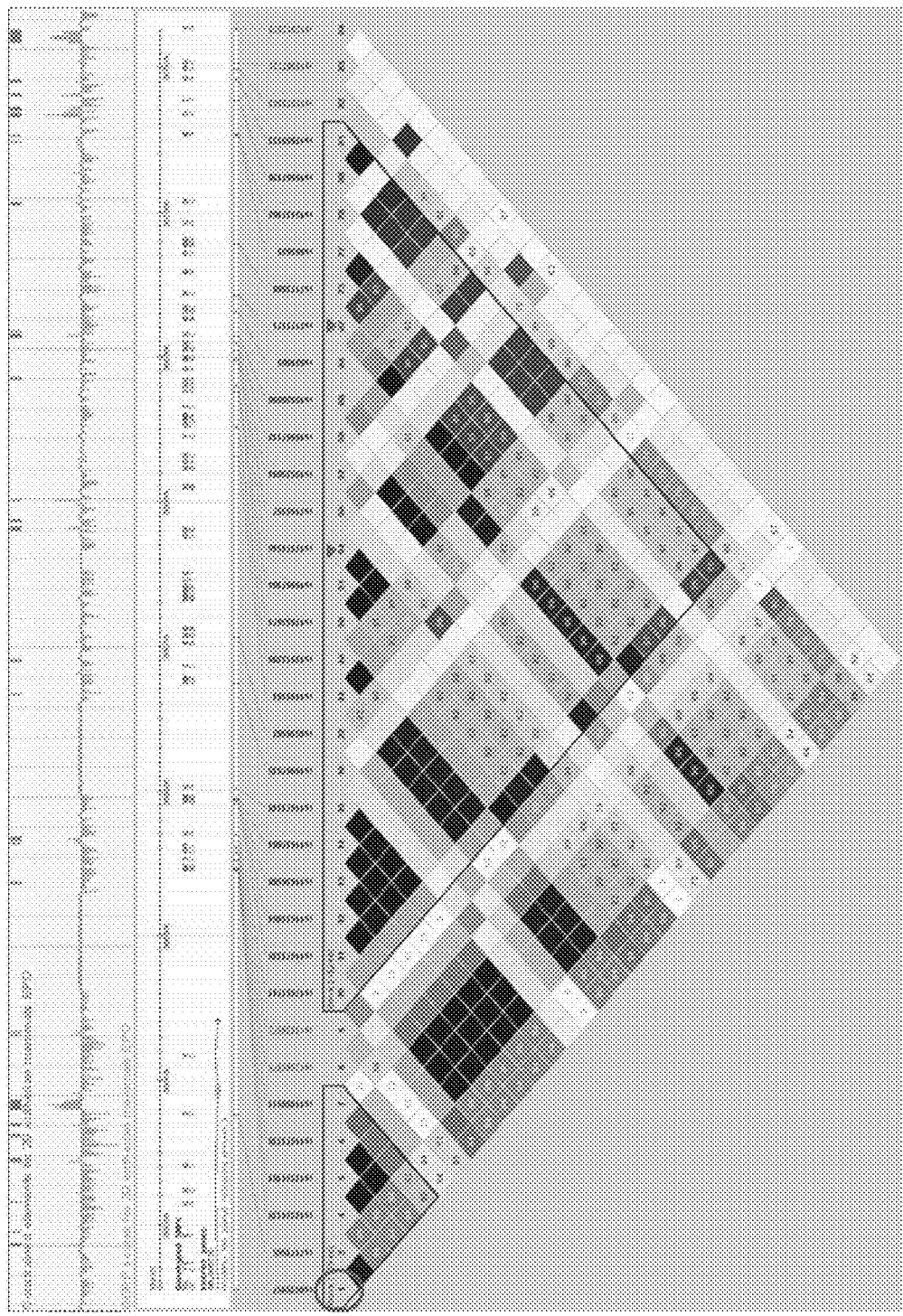
FIG. 1. The LD plot of the RASGRP1 SNPs, based on the HapMap European data. The top panel shows the constrained elements and conservation scores called by the DNA sequence alignments of 29 eutherian mammals (Ensembl, on the world wide web at .ensembl.org. See Cooper et al. *Genome Research* 2005; 15:901-913. The LD map is made by Haploview v4.0 software available on the world wide web at road.mit.edu/personal/jcbarret/haploview. D' values (%) are shown in the boxes, and $r^2$ values are represented by the grey scale. The red arrows highlight the SNPs genotyped in this study. Inside the red circle, it is the SNP described in Example I.

Type 1 diabetes (T1D) is a common and strongly heritable disease that most often manifests in childhood. Recent genome wide association studies have revealed a number of new genes associated with the disease. We carried out a follow-up strategy to our T1D GWA study in an attempt to uncover additional novel T1D risk loci. We selected 982 single nucleotide polymorphisms (SNPs) with at least a nominally significant P-value (but excluding SNPs in the major histocompatibility complex region) from a combination of our data generated on 563 T1D probands and 1,146 controls plus 483 complete T1D family trios of the same ancestry, using the Illumina HumanHap550 BeadChip. We then genotyped these SNPs in an independent cohort of 939 nuclear T1D families from Montreal and the type 1 diabetes genetics consortium. Subsequently, we looked across all three cohorts plus the Wellcome Trust Case Control Consortium dataset for T1D to identify SNPs in loci that were both not previously described and nominally significant across all cohorts. We selected five loci for further investigation, which we queried in T1D probands from the DCCT/EDIC study including 1,303 T1D patients using an independent matched control dataset of diabetes free individuals from Philadelphia which were genotyped on the 1M and HumanHap550K SNP BeadChips, respectively. Two of the five variants (rs9976767 and rs3757247) were also significantly associated with T1D in this cohort; these SNPs reside in the UBASH3A (OR: 1.16; five cohorts combined P=2.33× $10^{-8}$) and BACH2 (OR: 1.13; combined P=1.25×$10^{-6}$) genes respectively, both of which are biologically relevant to autoimmunity. In summary, we have identified two novel loci on 21q and 6q that are associated with T1D across five different cohorts of European decent.

The following definitions are provided to facilitate an understanding of the present invention:

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, Aisolated@ and Abiologically pure@ do not necessarily reflect the extent to which the compound has been purified. An isolated compound of the present invention can be obtained from its natural source, can be produced using laboratory synthetic techniques or can be produced by any such chemical synthetic route.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The phrase "Type 1 diabetes (T1D)" refers to a chronic (lifelong) disease that occurs when the pancreas produces too little insulin to regulate blood sugar levels appropriately. T1D, often called juvenile or insulin-dependent diabetes results from altered metabolism of carbohydrates (including sugars such as glucose), proteins, and fats. In type 1 diabetes, the beta cells of the pancreas produce little or no insulin, the hormone that allows glucose to enter body cells. Once glucose enters a cell, it is used as fuel. Without adequate insulin, glucose builds up in the bloodstream instead of going into the cells. The body is unable to use this glucose for energy despite high levels in the bloodstream, leading to increased hunger. In addition, the high levels of glucose in the blood cause the patient to urinate more, which in turn causes excessive thirst. Within 5 to 10 years after diagnosis, the insulin-producing beta cells of the pancreas are completely destroyed, and no more insulin is produced.

"T1D-associated SNP or specific marker" is a SNP or marker which is associated with an increased or decreased risk of developing TID not found normal patients who do not have this disease. Such markers may include but are not limited to nucleic acids, proteins encoded thereby, or other small molecules. Type 1 diabetes can occur at any age, but it usually starts in people younger than 30. Symptoms are usually severe and occur rapidly. The exact cause of type 1 diabetes is not known. Type 1 diabetes accounts for 3% of all new cases of diabetes each year. There is 1 new case per every 7,000 children per year. New cases are less common among adults older than 20.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose. "Sample" or "patient sample" or "biological sample" generally refers to a sample which may be tested for a particular molecule, preferably an T1D specific marker molecule, such as a marker shown in the tables provided below. Samples may include but are not limited to cells, body fluids, including blood, serum, plasma, urine, saliva, tears, pleural fluid and the like.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

"Linkage" describes the tendency of genes, alleles, loci or genetic markers to be inherited together as a result of their location on the same chromosome, and is measured by percent recombination (also called recombination fraction, or θ) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causative mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

"Target nucleic acid" as used herein refers to a previously defined region of a nucleic acid present in a complex nucleic acid mixture wherein the defined wild-type region contains at least one known nucleotide variation which may or may not be associated with T1D. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form. By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus, the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any T1D specific marker gene or nucleic acid, but does not hybridize to other human nucleotides. Also polynucleotide which Aspecifically hybridizes@ may hybridize only to a T1D specific marker, such a T1D-specific marker shown in Tables 1-3. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5''C + 16.6 \text{ Log } [Na+] + 0.41(\% \ G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide" or "oligo" as used herein means a short sequence of DNA or DNA derivatives typically 8 to 35 nucleotides in length, primers, or probes. An oligonucleotide can be derived synthetically, by cloning or by amplification. An oligo is defined as a nucleic acid molecule comprised of two or more ribo- or deoxyribonucleotides, preferably more than three. The exact size of the oligonucleotide will depend on various factors and on the particular application and use of the oligonucleotide. The term "derivative" is intended to include any of the above described variants when comprising an additional chemical moiety not normally a part of these molecules. These chemical moieties can have varying purposes including, improving solubility, absorption, biological half life, decreasing toxicity and eliminating or decreasing undesirable side effects.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting UBASH3A, GLIS3, RASGRP1, BACH2, and EDG7 mRNA may be between 15-35 nucleotides in length, and more typically about 21 nucleotides in length. Exemplary siRNA molecules which downregulate the aforementioned gene targets are provided in Tables 6-10.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and Atransduction@ refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, peptide-tethering, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the T1D specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the T1D specific marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene@ refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms Arecombinant organism," or Atransgenic organism@ refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase Aa recombinant organism@ encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term Aspecific binding pair@ is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long. "Sample" or "patient sample" or "biological sample" generally refers to a sample which may be tested for a particular molecule, preferably a T1D specific marker molecule, such as a marker shown in Tables 1-4. Samples may include but are not limited to cells, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, small molecules, antibodies, peptides, peptide/DNA complexes, and any nucleic acid based molecule, for example an oligo, which exhibits the capacity to modulate the activity of the SNP containing nucleic acids described herein or their encoded proteins. Agents are evaluated for potential biological activity by inclusion in screening assays described herein below.

The term "modulate" as used herein refers increasing or decreasing. For example, the term modulate refers to the ability of a compound or test agent to interfere with signaling or activity of a gene or protein of the present invention. Therefore, modulating the signaling mediated by the target genes disclosed herein (e.g., UBASH3A, GLIS3, RASGRP1, BACH2, and EDG7) means that an agent or compound inhibits or enhances the activity of the proteins encoded by the gene. This includes altering the activity of natural killer cells, and preventing autoimmune beta cell destruction.

Methods of Using T1D-Associated SNPs for T1D Detection Assays

T1D SNP containing nucleic acids, including but not limited to those listed in Tables 1-5, may be used for a variety of purposes in accordance with the present invention. T1D-associated SNP containing DNA, RNA, or fragments thereof may be used as probes to detect the presence of and/or expression of T1D specific markers. Methods in which T1D specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting T1D-associated SNPs may be conducted on any type of biological sample, including but not limited to body fluids (including blood, urine, serum, gastric lavage), any type of cell (such as white blood cells, mononuclear cells) or body tissue.

From the foregoing discussion, it can be seen that T1D associated SNP containing nucleic acids, vectors expressing the same, T1D SNP containing marker proteins and anti-T1D specific marker antibodies of the invention can be used to detect T1D associated SNPs in body tissue, cells, or fluid, and alter T1D SNP containing marker protein expression for purposes of assessing the genetic and protein interactions involved in T1D.

In most embodiments for screening for T1D-associated SNPs, the T1D-associated SNP containing nucleic acid in the sample will initially be amplified, e.g. using PCR, to increase the amount of the template as compared to other sequences present in the sample. This allows the target sequences to be detected with a high degree of sensitivity if they are present in the sample. This initial step may be avoided by using highly sensitive array techniques that are becoming increasingly important in the art.

Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus, any of the aforementioned techniques may be used to detect or quantify T1D-associated SNP marker expression and accordingly, detect patient susceptibility for developing T1D.

Kits and Articles of Manufacture

Any of the aforementioned products can be incorporated into a kit which may contain an T1D-associated SNP specific marker polynucleotide or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Methods of Using T1D-Associated SNPs for Development of Therapeutic Agents

Since the SNPs identified herein have been associated with the etiology of T1 D, methods for identifying agents that modulate the activity of the genes and their encoded products containing such SNPs should result in the generation of efficacious therapeutic agents for the treatment of a variety of disorders associated with this condition.

Chromosomes 21, 6, 15, 9 and 1 contain regions which provide suitable targets for the rational design of therapeutic agents which modulate the activity of proteins encoded by these sequences. Small nucleic acid molecules or peptides corresponding to these regions may be used to advantage in the design of therapeutic agents which effectively modulate the activity of the encoded proteins.

Molecular modeling should facilitate the identification of specific organic molecules with capacity to bind to the active site of the proteins encoded by the SNP containing nucleic acids based on conformation or key amino acid residues required for function. A combinatorial chemistry approach will be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Alternatively, primary cells may be isolated from donors expressing the minor or major SNP alleles associated with the T1D described herein. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered T1D associated gene. These host cell lines or cells are defective at the polypeptide level. The host cell lines or cells are grown in the presence of drug compound. The rate of cellular metabolism of the host cells is measured to determine if the compound is capable of regulating cellular metabolism in the defective cells. Host cells contemplated for use in the present invention include but are not limited to bacterial cells, fungal cells, insect cells, mammalian cells, and plant cells. The T1D-associated SNP encoding DNA molecules may be introduced singly into such host cells or in combination to assess the phenotype of cells conferred by such expression. Alternatively, donor cells expressing the alleles described herein may be employed. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

Cells and cell lines suitable for studying the effects of the SNP encoding nucleic acids on glucose metabolism and methods of use thereof for drug discovery are provided. Such cells and cell lines will either already express the SNP or be transfected with the SNP encoding nucleic acids described herein and the effects on glucagon secretion, insulin secretion and/or beta cell apoptosis can be determined. Such cells and cell lines will also be contacted with the siRNA molecules provided herein to assess the effects thereof on glucagon secretion, insulin secretion and/or beta cell apoptosis. The siRNA molecules will be tested alone and in combination of 2, 3, 4, and 5 siRNAs to identify the most efficacious combination for down regulating at least one target gene, e.g., UBASH3A, GLIS3, RASGRP1, BACH2, and EDG7. Cells suitable for these purposes include, without limitation, INS cells (ATCC CRL 11605), PC 12 cells (ATCC CRL 1721), MIN6 cells, alpha-TC6 cells and INS-1 832/13 cells (Fernandez et al., J. of Proteome Res. (2007). 7:400-411). Pancreatic islet cells can be isolated and cultured as described in Joseph, J. et al., (J. Biol. Chem. (2004) 279:51049). Diao et al. (J. Biol. Chem. (2005) 280:33487-33496), provide methodology for assessing the effects of the SNP encoding nucleic acids and/or the siRNAs provided herein on glucagon secretion and insulin secretion. Park, J. et al. (J. of Bioch. and Mol. Biol. (2007) 40:1058-68) provide methodology for assessing the effect of these nucleic acid molecules on glucosamine induced beta cell apoptosis in pancreatic islet cells.

A wide variety of expression vectors are available that can be modified to express the novel DNA or RNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/ V5&His (Invitrogen); baculovirus vectors such as pVL1392, pVL1393, or pAC360 (Invitrogen); and yeast vectors such as YRP17, YIPS, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter, as well as neuronal-specific platelet-derived growth factor promoter (PDGF), and the Thy-1 promoter.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the T1D-associated SNPs of the present invention or functional fragments thereof provide a system in which to screen potential compounds or agents for the ability to modulate the development of T1D. Thus, in one embodiment, the nucleic acid molecules of the invention may be used to create recombinant cell lines for use in assays to identify agents which modulate aspects of the diabetic phenotype. Also provided herein are methods to screen for compounds capable of modulating the function of proteins encoded by the SNP containing nucleic acids described below.

Another approach entails the use of phage display libraries engineered to express fragment of the polypeptides encoded by the SNP containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacophore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacophore.

Thus, one may design drugs which have, e.g., improved polypeptide activity or stability or which act as inhibitors, agonists, antagonists, etc. of polypeptide activity. By virtue of the availability of SNP containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of T1D-associated SNP containing nucleic acids enables the production of strains of laboratory mice carrying the T1D-associated SNPs of the invention. Transgenic mice expressing the T1D-associated SNP of the invention provide a model system in which to examine the role of the protein encoded by the SNP containing nucleic acid in the development and progression towards T1D. Methods of introducing transgenes in laboratory mice are known to those of skill in the art. Three common methods include: (1) integration of retroviral vectors encoding the foreign gene of interest into an early embryo; (2) injection of DNA into the pronucleus of a newly fertilized egg; and (3) the incorporation of genetically manipulated embryonic stem cells into an early embryo. Production of the transgenic mice described above will facilitate the molecular elucidation of the role that a target protein plays in various cellular metabolic processes, including: aberrant lipid deposition, altered cellular metabolism and glucose regulation. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of T1D-associated SNP containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated T1D-associated SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Non-homologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing T1D-associated SNP containing nucleic acid as a targeted insertional cassette provides means to detect a successful insertion as visualized, for example, by acquisition of immunoreactivity to an antibody immunologically specific for the polypeptide encoded by T1D-associated SNP nucleic acid and, therefore, facilitates screening/selection of ES cells with the desired genotype.

As used herein, a knock-in animal is one in which the endogenous murine gene, for example, has been replaced with human T1D-associated SNP containing gene of the invention. Such knock-in animals provide an ideal model system for studying the development of T1D.

As used herein, the expression of a T1D-associated SNP containing nucleic acid, fragment thereof, or a T1D-associated SNP fusion protein can be targeted in a "tissue specific manner" or "cell type specific manner" using a vector in which nucleic acid sequences encoding all or a portion of T1D-associated SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific expression of proteins are well known in the art and described herein.

The nucleic acid sequence encoding the T1D-associated SNP of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; and Glial fibrillar acidic protein (GFAP) promoter for the expression of transgenes in glial cells.

Methods of use for the transgenic mice of the invention are also provided herein. Transgenic mice into which a nucleic acid containing the T1D-associated SNP or its encoded protein have been introduced are useful, for example, to develop screening methods to screen therapeutic agents to identify those capable of modulating the development of T1D.

Pharmaceuticals and Peptide Therapies

The elucidation of the role played by the T1D associated SNPs described herein in cellular metabolism facilitates the development of pharmaceutical compositions useful for treatment and diagnosis of T1D. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

As it is presently understood, RNA interference involves a multi-step process. Double stranded RNAs are cleaved by the endonuclease Dicer to generate nucleotide fragments (siRNA). The siRNA duplex is resolved into 2 single stranded RNAs, one strand being incorporated into a protein-containing complex where it functions as guide RNA to direct cleavage of the target RNA (Schwarz et al, Mol. Cell.

10:537 548 (2002), Zamore et al, Cell 101:25 33 (2000)), thus silencing a specific genetic message (see also Zeng et al, Proc. Natl. Acad. Sci. 100:9779 (2003)).

The invention includes a method of treating T1D in a mammal. An exemplary method entails administering to the mammal a pharmaceutically effective amount of an siRNA molecule directed to a gene target selected from the group consisting of UBASH3A (GenBank No.: NM_018961; SEQ ID NO: 1), GLIS3, (GenBank No.: NM_001042413; SEQ ID NO: 2), RASGRP1 (GenBank No.: NM_005739; SEQ ID NO: 3), BACH2 (GenBank No.: NM_021813; SEQ ID NO: 4) and EDG7 (GenBank Acc. No.: AY322547; SEQ ID NO: 5). The siRNA inhibits the expression of the aforementioned genes. Preferably, the mammal is a human. The term "patient" as used herein refers to a human.

Specific siRNA preparations directed at inhibiting the expression of UBASH3A, GLIS3, RASGRP1, BACH2 and EDG7, as well as delivery methods are provided as a novel therapy to treat T1D. See Tables 6-10. The siRNA can be delivered to a patient in vivo either systemically or locally with carriers, as discussed below. The compositions of the invention may be used alone or in combination with other agents or genes encoding proteins to augment the efficacy of the compositions.

A "membrane permeant peptide sequence" refers to a peptide sequence which is able to facilitate penetration and entry of the siRNA inhibitor across the cell membrane. Exemplary peptides include with out limitation, the signal sequence from Karposi fibroblast growth factor exemplified herein, the HIV tat peptide (Vives et al., J Biol. Chem., 272:16010-16017, 1997), Nontoxic membrane translocation peptide from protamine (Park et al., FASEB J. 19(11):1555-7, 2005), CHARIOT® delivery reagent (Active Motif; U.S. Pat. No. 6,841,535) and the antimicrobial peptide Buforin 2.

In one embodiment of the invention siRNAs are delivered for therapeutic benefit. There are several ways to administer the siRNA of the invention to in vivo to treat T1D including, but not limited to, naked siRNA delivery, siRNA conjugation and delivery, liposome carrier-mediated delivery, polymer carrier delivery, nanoparticle compositions, plasmid-based methods, and the use of viruses.

siRNA composition of the invention can comprise a delivery vehicle, including liposomes, for administration to a subject, carriers and diluents and their salts, and/or can be present in pharmaceutically acceptable formulations. This can be necessary to allow the siRNA to cross the cell membrane and escape degradation. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995; Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192; Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

The frequency of administration of the siRNA to a patient will also vary depending on several factors including, but not limited to, the type and severity of the T1D to be treated, the route of administration, the age and overall health of the individual, the nature of the siRNA, and the like. It is contemplated that the frequency of administration of the siRNA to the patient may vary from about once every few months to about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate siRNA, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate siRNA to a patient according to the methods of the invention. The use of nanoparticles to deliver siRNAs, as well as cell membrane permeable peptide carriers that can be used are described in Crombez et al., Biochemical Society Transactions v35:p44 (2007).

Methods of the invention directed to treating T1D involve the administration of at least one UBASH3A, GLIS3, RASGRP1, BACH2 and EDG7 siRNA in a pharmaceutical composition. The siRNA is administered to an individual as a pharmaceutical composition comprising the siRNA and a pharmaceutically acceptable carrier. Pharmaceutically acceptable carriers are well known in the art and include aqueous solutions such as physiologically buffered saline, other solvents or vehicles such as glycols, glycerol, oils such as olive oil or injectable organic esters.

A pharmaceutically acceptable carrier can contain physiologically acceptable compounds that act, for example, to stabilize the siRNA or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the siRNA.

One skilled in the art appreciates that a pharmaceutical composition comprising siRNA can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intra-tracheally (i.t.), or intra-articularly or by passive or facilitated absorption. The same routes of administration can be used other pharmaceutically useful compounds, for example, small molecules, nucleic acid molecules, peptides, antibodies and polypeptides as discussed hereinabove.

A pharmaceutical composition comprising siRNA inhibitor also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer.

The pharmaceutical preparation comprises a siRNA targeting the SNP containing sequences described herein or an expression vector encoding for the siRNA. Such pharmaceutical preparations can be administered to a patient for treating T1D.

Expression vectors for the expression of siRNA molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

A formulated siRNA composition can be a composition comprising one or more siRNA molecules or a vector encoding one or more siRNA molecules independently or in combination with a cationic lipid, a neutral lipid, and/or a polyethyleneglycol-diacylglycerol (PEG-DAG) or PEG-cholesterol (PEG-Chol) conjugate. Non-limiting examples of expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500-505.

A lipid nanoparticle composition is a composition comprising one or more biologically active molecules independently or in combination with a cationic lipid, a neutral lipid, and/or a polyethyleneglycol-diacylglycerol (i.e., polyethyleneglycol diacylglycerol (PEG-DAG), PEG-cholesterol, or PEG-DMB) conjugate. In one embodiment, the biologically active molecule is encapsulated in the lipid nanoparticle as a result of the process of providing and aqueous solution comprising a biologically active molecule of the invention (i.e., siRNA), providing an organic solution comprising lipid nanoparticle, mixing the two solutions, incubating the solutions, dilution, ultrafiltration, resulting in concentrations suitable to produce nanoparticle compositions.

Nucleic acid molecules can be administered to cells by incorporation into other vehicles, such as biodegradable polymers, hydrogels, cyclodextrins. (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722)

Cationic lipids and polymers are two classes of non-viral siRNA delivery which can form complexes with negatively charged siRNA. The self-assembly PEG-ylated polycation polyethylenimine (PEI) has also been used to condense and protect siRNAs (Schiffelers et al., 2004, Nuc. Acids Res. 32: 141-110). The siRNA complex can be condensed into a nanoparticle to allow efficient uptake of the siRNA through endocytosis. Also, the nucleic acid-condensing property of protamine has been combined with specific antibodies to deliver siRNAs and can be used in the invention (Song et al., 2005, Nat Biotech. 23:709-717).

In order to treat an individual having T1D, to alleviate a sign or symptom of the disease, siRNA should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of siRNA required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having T1D.

The effective dose of siRNA will depend on the mode of administration, and the weight of the individual being treated. The dosages described herein are generally those for an average adult but can be adjusted for the treatment of children. The dose will generally range from about 0.001 mg to about 1000 mg.

The concentration of siRNA in a particular formulation will depend on the mode and frequency of administration. A given daily dosage can be administered in a single dose or in multiple doses so long as the siRNA concentration in the formulation results in the desired daily dosage. One skilled in the art can adjust the amount of siRNA in the formulation to allow administration of a single dose or in multiple doses that provide the desired concentration of siRNA over a given period of time.

In an individual suffering from T1D, in particular a more severe form of the disease, administration of siRNA can be particularly useful when administered in combination, for example, with a conventional agent for treating such a disease. The skilled artisan would administer siRNA, alone or in combination and would monitor the effectiveness of such treatment using routine methods such as pancreatic beta cell function determination, radiologic, immunologic or, where indicated, histopathologic methods. Other conventional agents for the treatment of diabetes include insulin administration, glucagon administration or agents that alter levels of either of these two molecules. Glucophage®, Avandia®, Actos®, Januvia® and Glucovance® are examples of such agents.

Administration of the pharmaceutical preparation is preferably in an "effective amount" this being sufficient to show benefit to the individual. This amount prevents, alleviates, abates, or otherwise reduces the severity of T1D symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

The methods set forth below are provided to facilitate the practice of the present invention.

Signal Distillation

We selected SNPs with at least a nominally significant combined P-value (major histocompatibility complex region excluded) from our genome wide genotype data generated on Caucasians from 563 T1D probands and 1,146 controls plus 483 complete T1D family trios, using the Illumina HumanHap550 BeadChip. We then genotyped these SNPs using the Illumina GoldenGate platform in an independent cohort of 939 nuclear T1D families from Montreal and the type 1 diabetes genetics consortium (T1DGC). Subsequently we looked across all three cohorts plus the publicly available Wellcome Trust Case Control Consortium (WTCCC) dataset on the world wide web at wtccc.org.uk[17] for T1D to identify SNPs in loci that were both not previously described and nominally significant across all cohorts. We selected five loci for further investigation, which we queried in T1D probands from the DCCT/EDIC study using an independent matched control dataset from Philadelphia which were genotyped on the Illumina 1M and HumanHap550K BeadChips, respectively.

Subjects

1. Type 1 Diabetes Cohort from Canada:

The Canadian cohort consisted of 1,120 nuclear family trios (one affected child and two parents) and 267 independent T1D cases, collected in pediatric diabetes clinics in Montreal, Toronto, Ottawa and Winnipeg. The median age at onset is 8 with lower and upper quartiles at 4.6 years and 11 years. All patients were diagnosed under the age of 18, were treated with insulin since diagnosis and none has stopped treatment for any reason since. Disease diagnosis was based on these clinical criteria, rather than any laboratory tests. Ethnic backgrounds were of mixed European descent, with the largest single subset (409 families) being French Canadian. The Research Ethics Board of the Montreal Children's Hospital and other participating centers approved the study, and written informed consent was obtained from all subjects.

2. Type 1 Diabetes Genetics Consortium Cohort:

The Type 1 Diabetes Genetics Consortium cohort consisted of 549 families (2350 individuals) with at least two children diagnosed with diabetes and both parents available as of the July 2005 data freeze. Criteria were age at diagnosis below 35 years and uninterrupted treatment with insulin within six months of diagnosis. For siblings of probands diagnosed under the age of 35, the age-at-diagnosis limit was extended to 45 if they were lean and had positive antibodies and/or low C-peptide levels at diagnosis. The median age is 8 with quartiles at 4 years and 13 years. The samples were collected in Europe, North America and Australia and most subjects were of European ancestry. Autoantibody results are available but were not used to substantiate the diagnosis, except as noted above.

3. Type 1 Diabetes Cohort from Philadelphia:

The T1D cohort consisted of 103 children recruited at the Children's Hospital of Philadelphia (CHOP), since September, 2006. All patients were diagnosed under the age of 18. Of those, 49 T1D patients (32 female, 17 male) were Caucasians by self-report (average age of onset 7.07 years; range 9 months-14 years) and were included in the analysis. All were treated with insulin since diagnosis and none has stopped treatment for any reason since. The Research Ethics Board of CHOP approved the study and written informed consent was obtained from all subjects.

4. The Diabetes Control and Complications Trial/Epidemiology of Diabetes

Complications and Interventions (DCCT/EDIC) Type 1 diabetes cohort: The DCCT was a multi-center randomized clinical trial to determine the effect of intensive insulin treatment with respect to reduced development and progression of retinopathy and nephropathy complications in patients with type 1 diabetes[19,20]. A total of 1,441 subjects with type 1 diabetes were recruited from 29 centers across North America into the DCCT between 1983 and 1989; they were between 13 and 39 years of age and 53% were male. They were recruited into two cohorts: the primary prevention cohort consisted of 726 subjects with no retinopathy, an albumin excretion rate <28 μg per minute, and diabetes duration of 1 to 5 years and were used to determine if intensive therapy prevented the development of diabetic retinopathy in patients with no retinopathy; the secondary intervention cohort consisted of 715 subjects who had non-proliferative retinopathy, a urinary albumin excretion rate <140 μg per minute, and diabetes duration of 1 to 15 years were studied to determine whether intensive therapy would affect the progression of early retinopathy[19]. Approval for the DCCT/EDIC Genetics study was provided by the Research Ethics Board of the Hospital for Sick Children, Toronto.

The Illumina 1M assay was genotyped on all available probands. To detect and remove outliers due to population stratification from the majority self-reported white probands Eigenstrat[21] was used to select probands by sequential analysis. After exclusions of outliers, there were 1303 DCCT/EDIC probands, (695 male, 608 females) with mean age of diagnosis of T1D of 21 years (SD=8, range 0-38).

5. Control Subjects from Philadelphia:

The control group included 1,146 children with self reported Caucasian status, mean age 9.42 years; 53.05% male and 46.95% female, who did not have diabetes or a first-degree relative with T1D. The control group used to match with the 1,100 DCCT/EDIC T1D probands included 2,024 children with self reported Caucasian ethnicity, mean age 8.82 years; 50.83% male and 49.17% female, who did not have diabetes or a first-degree relative with T1D. These individual were recruited by CHOP's clinicians and nursing staff within the CHOP's Health Care Network, including four primary care clinics and several group practices and outpatient practices that included well child visits. Of these 2024 individuals, 1673 were selected using population stratification analysis from eigenstrat, similar to that described above for DCCT/EDIC probands (868 males, 801 females, 4 with ambiguous gender). The Research Ethics Board of CHOP approved the study, and written informed consent was obtained from all subjects.

Genotyping

Genotypes for this study were obtained using the Infinium and GoldenGate platforms from Illumina. We performed high throughput genome-wide SNP genotyping, using the Illumina Infinium™ II HumanHap550 BeadChip technology[1,2] (Illumina, San Diego), at the Center for Applied Genomics at CHOP. We used 750 ng of genomic DNA to genotype each sample, according to the manufacturer's guidelines. DCCT/EDIC samples were genotyped on the Illumina 1M chip at Illumina (San Diego, Calif.).

Statistics

All statistical tests for association were carried out using the software package plink[22]. The single marker analysis for the genome-wide data was carried out using a $\chi^2$ test on allele count differences between 563 cases and 1,146 controls. Odds ratios and the corresponding 95% confidence intervals were calculated for the association analysis. The transmission disequilibrium test was used to calculate P-values on differences between transmitted and untransmitted allele counts in the T1D trios and nuclear families. Counts of untransmitted and transmitted alleles from heterozygous parents to affected offspring were determined using the standard transmission disequilibrium test implemented in the Haploview software package[4]. The P-values from the case-control and family-based analyses in our three discovery cohorts were combined using Fisher's method[5] to quantify the overall evidence for association.

The following examples are provided to illustrate certain embodiments of the invention. They are not intended to limit the invention in any way.

Example I

Gentic Loci Associated with TID

Type 1 diabetes (T1D) is a multifactorial disease with a strong genetic component that results from autoimmune destruction of the pancreatic β-cells. The major T1D susceptibility locus, mapping to the HLA class II genes at 6p21[1] and encoding highly polymorphic antigen-presenting proteins, accounts for almost 50% of the genetic risk for T1D[2]. Several other loci with more modest effects account for another 10-20% of the risk. These include: (1) the insulin (INS) VNTR[3], modulating thymic expression of and tolerance to insulin, a major T1D autoantigen[4,5]; (2) the Arg620Trp single-nucleotide polymorphism (SNP) at PTPN22, which affects the function of a negative regulator of TCR signaling[6]; (3) Non-coding SNPs at IL2RA[7-9], which encodes the a chain of the IL2 receptor complex (CD25), an important modulator of immunity; (4) variants in the CTLA4 locus[10] whose protein product transmits inhibitory signals to attenuate T-cell activation. It is worth noting that all of these T1D-associated genes are expressed in cells with immune function and all except INS have been associated with other autoimmune disorders.

The recent development of high throughput single nucleotide polymorphism (SNP) genotyping array technologies has enabled us[11] and others[12,13] to perform genome-wide association (GWA) studies in search of the remaining T1D loci. The first successful use in T1D involved screening of 12,000 nonsynonymous SNPs, which found T1D association with rs1990760, involving an Ala946Thr substitution on the IFIH1 gene (Interferon-Induced with Helicase C domain 1)[14]. We recently reported the outcome of our GWA for T1D where we examined a large pediatric T1D cohort of European decent followed by a successful TDT replication attempt in an independent cohort[15]. In addition to confirming the previously identified loci, we observed highly significant association with KIAA0350, the gene product of which has been recently renamed C-type lectin domain family 16 member A (CLEC16A); subsequent follow-up of our data also revealed a locus on 12q13[16]. The Wellcome Trust Case Control Consortium[17] also demonstrated association to the same regions of 16p13 and 12q13 which they subsequently followed up and replicated[18], along with other loci on 12q24 and 18p11.

We carried out a follow-up strategy to uncover additional novel T1D risk loci. Here, we describe two loci that were significantly associated with T1D during this process, both of which reside in genes that are biologically relevant to autoimmunity. These genes encode ubiquitin-associated and SH3 domain-containing protein A (UBASH3A) and BTB and CNC homology 2 (BACH2), respectively, both of which are known to be involved in T cell signaling.

From a combination of our genotyping data generated on T1D probands and controls plus T1D family trios of the same ancestry, we selected 982 SNPs that fulfilled the two criteria of not residing in the major histocompatibility complex and being at least nominally significantly associated with T1D. We then took those SNPs forward with additional genotyping in an independent cohort of nuclear T1D families from Montreal and the T1DGC. As shown in Table 1, thirty three single point associations were at least nominally significant across all four cohorts utilized for the discovery stage of this process. However, the bulk of them had been previously reported and were therefore not novel i.e. they resided at the well-established PTPN22[6], 12q13[16,18], KIAA0350[15,18], IL2RA[7-9], CTLA4[10] and IFIH1[14] loci. However, six SNPs residing at five loci fulfilled our criteria for further replication efforts.

TABLE 1

Cohort datasets leveraged in selection of candidate loci for further replication efforts. The six SNPs indicated in bold represent novel associations deemed appropriate for further investigation. Minor allele frequencies, P-values and odds ratios (OR) are shown. Combined P-values for the three discovery cohorts are also shown, together with the gene in which the markers resides or which they are nearest to. P-values are two-sided in each instance. Aff allele freq, allele frequency in affected individuals; Ctrl allele freq, allele frequency in unaffected individuals; Trans:untrans, ratio of transmitted to untransmitted allele. *gene not previously implicated in T1D.

| Chr | SNP | Position | T1D families - Montreal and T1DGC | | | Case-Control Cohort | | | | | T1D family trios | | | Combined P | WTCCC | | | | Gene |
|---|---|---|---|---|---|---|---|---|---|---|---|---|---|---|---|---|---|---|---|
| | | | Trans:untrans | OR | TDT P-value | Trans:untrans | Aff allele freq | Ctrl allele freq | P | OR | Trans:untrans | OR | TDT P-value | | Aff allele freq | Ctrl allele freq | P | OR | |
| 1 | rs2358994 | 114230984 | 398:287 | 1.387 | $2.22 \times 10^{-5}$ | | 0.232 | 0.175 | $7.11 \times 10^{-5}$ | 1.426 | 181:127 | 1.425 | 0.0021 | $1.25 \times 10^{-9}$ | 0.246 | 0.179 | $4.05 \times 10^{-16}$ | 1.504 | PTPN22 |
| 1 | rs12566340 | 114221851 | 492:379 | 1.298 | $1.29 \times 10^{-4}$ | | 0.288 | 0.237 | 0.0015 | 1.293 | 212:164 | 1.293 | 0.013 | $5.53 \times 10^{-7}$ | 0.287 | 0.226 | $1.09 \times 10^{-11}$ | 1.377 | PTPN22 |
| 1 | rs7529353 | 114221985 | 474:354 | 1.339 | $3.04 \times 10^{-5}$ | | 0.294 | 0.242 | $9.75 \times 10^{-4}$ | 1.309 | 218:165 | 1.321 | 0.0068 | $5.47 \times 10^{-8}$ | 0.287 | 0.227 | $2.69 \times 10^{-11}$ | 1.368 | PTPN22 |
| 1 | rs1230661 | 113987113 | 456:331 | 1.378 | $8.36 \times 10^{-6}$ | | 0.267 | 0.216 | $8.75 \times 10^{-4}$ | 1.324 | 209:161 | 1.298 | 0.013 | $2.68 \times 10^{-7}$ | 0.276 | 0.217 | $3.34 \times 10^{-11}$ | 1.371 | PTPN22 |
| 1 | rs1217407 | 114195271 | 505:395 | 1.278 | $2.46 \times 10^{-4}$ | | 0.298 | 0.244 | $7.42 \times 10^{-4}$ | 1.316 | 225:168 | 1.339 | 0.004 | $1.79 \times 10^{-7}$ | 0.298 | 0.240 | $1.70 \times 10^{-10}$ | 1.344 | PTPN22 |
| 1 | rs4839335 | 114035394 | 482:354 | 1.362 | $9.56 \times 10^{-6}$ | | 0.3 | 0.25 | 0.002 | 1.285 | 224:172 | 1.302 | 0.009 | $4.66 \times 10^{-8}$ | 0.299 | 0.241 | $2.81 \times 10^{-10}$ | 1.339 | PTPN22 |
| 12 | rs10876864 | 54687352 | 631:528 | 1.195 | 0.0025 | | 0.458 | 0.388 | $8.39 \times 10^{-5}$ | 1.336 | 265:188 | 1.41 | $2.97 \times 10^{-4}$ | $1.86 \times 10^{-8}$ | 0.475 | 0.414 | $2.04 \times 10^{-9}$ | 1.283 | 12q13 |
| 12 | rs1701704 | 54698754 | 549:425 | 1.292 | $7.09 \times 10^{-5}$ | | 0.379 | 0.303 | $9.89 \times 10^{-6}$ | 1.402 | 245:180 | 1.361 | 0.0016 | $4.61 \times 10^{-10}$ | 0.397 | 0.339 | $5.91 \times 10^{-9}$ | 1.282 | 12q13 |
| 16 | rs2041670 | 11082153 | 384:444 | 0.865 | 0.037 | | 0.265 | 0.345 | $2.01 \times 10^{-6}$ | 0.682 | 172:233 | 0.738 | 0.0024 | $5.00 \times 10^{-8}$ | 0.264 | 0.315 | $7.05 \times 10^{-8}$ | 0.781 | KIAA0350 |
| 16 | rs725613 | 11077184 | 397:465 | 0.854 | 0.021 | | 0.3 | 0.39 | $3.24 \times 10^{-7}$ | 0.672 | 178:248 | 0.718 | $6.95 \times 10^{-4}$ | $1.70 \times 10^{-9}$ | 0.292 | 0.340 | $3.90 \times 10^{-7}$ | 0.797 | KIAA0350 |
| 12 | rs11171710 | 54654345 | 464:574 | 0.808 | $6.40 \times 10^{-4}$ | | 0.405 | 0.462 | 0.0016 | 0.792 | 197:244 | 0.807 | 0.025 | $4.32 \times 10^{-6}$ | 0.404 | 0.452 | $2.40 \times 10^{-6}$ | 0.821 | 12q13 |
| 10 | rs7072793 | 6146272 | 574:507 | 1.132 | 0.042 | | 0.486 | 0.41 | $2.96 \times 10^{-5}$ | 1.34 | 268:200 | 1.34 | 0.0017 | $4.54 \times 10^{-7}$ | 0.455 | 0.409 | $6.24 \times 10^{-6}$ | 1.207 | IL2RA |
| 10 | rs7073236 | 6146558 | 566:464 | 1.22 | 0.0015 | | 0.487 | 0.414 | $5.67 \times 10^{-5}$ | 1.343 | 264:196 | 1.347 | 0.0015 | $3.62 \times 10^{-8}$ | 0.455 | 0.409 | $7.31 \times 10^{-6}$ | 1.205 | IL2RA |
| 10 | rs3118470 | 6141719 | 504:431 | 1.169 | 0.017 | | 0.365 | 0.306 | $4.62 \times 10^{-4}$ | 1.308 | 240:181 | 1.326 | 0.004 | $5.29 \times 10^{-6}$ | 0.361 | 0.319 | $1.32 \times 10^{-5}$ | 1.208 | IL2RA |
| 16 | rs1035089 | 10955851 | 517:451 | 1.146 | 0.034 | | 0.48 | 0.42 | $8.25 \times 10^{-4}$ | 1.277 | 265:212 | 1.25 | 0.015 | $5.25 \times 10^{-5}$ | 0.482 | 0.439 | $2.59 \times 10^{-5}$ | 1.190 | KIAA0350 |
| 2 | rs231726 | 204449111 | 502:427 | 1.176 | 0.014 | | 0.358 | 0.321 | 0.028 | 1.184 | 228:177 | 1.288 | 0.011 | $4.00 \times 10^{-4}$ | 0.372 | 0.332 | $5.10 \times 10^{-5}$ | 1.191 | CTLA4 |
| 2 | rs1990760 | 162832297 | 422:518 | 0.815 | 0.0017 | | 0.398 | 0.434 | 0.048 | 0.864 | 203:251 | 0.809 | 0.024 | $2.00 \times 10^{-4}$ | 0.350 | 0.389 | $8.73 \times 10^{-5}$ | 0.845 | IFIH1 |
| 10 | rs706779 | 6138830 | 424:506 | 0.838 | 0.0072 | | 0.425 | 0.492 | $2.60 \times 10^{-4}$ | 0.764 | 185:257 | 0.72 | $6.16 \times 10^{-4}$ | $2.68 \times 10^{-7}$ | 0.419 | 0.458 | 0.00012 | 0.852 | IL2RA |
| 2 | rs926169 | 204430997 | 521:459 | 1.135 | 0.048 | | 0.426 | 0.38 | 0.0094 | 1.212 | 236:191 | 1.236 | 0.029 | 0.001 | 0.440 | 0.402 | 0.00022 | 1.167 | CTLA4 |
| 2 | rs1024161 | 204429997 | 534:462 | 1.156 | 0.023 | | 0.439 | 0.397 | 0.02 | 1.191 | 222:173 | 1.283 | 0.014 | $5.00 \times 10^{-4}$ | 0.441 | 0.403 | 0.00024 | 1.166 | CTLA4 |
| 16 | rs13330041 | 10996309 | 291:345 | 0.844 | 0.032 | | 0.172 | 0.246 | $1.01 \times 10^{-5}$ | 0.637 | 145:183 | 0.792 | 0.036 | $2.72 \times 10^{-7}$ | 0.175 | 0.204 | 0.00028 | 0.825 | KIAA0350 |
| 16 | rs16673553 | 11149407 | 319:387 | 0.824 | 0.01 | | 0.202 | 0.279 | $1.30 \times 10^{-5}$ | 0.655 | 146:203 | 0.719 | 0.0023 | $9.89 \times 10^{-9}$ | 0.217 | 0.249 | 0.00031 | 0.838 | KIAA0350 |
| 2 | rs2111485 | 162818782 | 417:500 | 0.834 | 0.0061 | | 0.393 | 0.433 | 0.027 | 0.849 | 210:254 | 0.827 | 0.041 | $6.00 \times 10^{-4}$ | 0.359 | 0.395 | 0.00034 | 0.858 | IFIH1 |
| 2 | rs12029644 | 114338303 | 222:172 | 1.291 | 0.012 | | 0.136 | 0.105 | 0.008 | 1.343 | 120:80 | 1.5 | 0.0047 | $5.42 \times 10^{-5}$ | 0.130 | 0.109 | 0.0018 | 1.218 | PTPN22 |
| 21 | rs9976767 | 42709459 | 571:504 | 1.13 | 0.041 | | 0.474 | 0.437 | 0.038 | 1.164 | 260:203 | 1.281 | 0.008 | 0.001 | 0.493 | 0.461 | 0.002 | 1.135 | UBASH3A* |
| 9 | rs10758593 | 4282083 | 539:462 | 1.17 | 0.015 | | 0.492 | 0.426 | | 1.303 | 254:209 | 1.215 | 0.037 | $2.25 \times 10^{-5}$ | 0.440 | 0.410 | 0.004 | 1.129 | GLIS3* |
| 9 | rs10758594 | 4285583 | 535:456 | 1.17 | 0.012 | | 0.513 | 0.451 | $6.66 \times 10^{-4}$ | 1.282 | 253:209 | 1.211 | 0.041 | $4.17 \times 10^{-5}$ | 0.456 | 0.427 | 0.004 | 1.127 | GLIS3* |
| 16 | rs7520320 | 114336816 | 211:169 | 1.249 | 0.031 | | 0.136 | 0.107 | 0.013 | 1.315 | 128:82 | 1.512 | 0.0034 | $1.00 \times 10^{-4}$ | 0.134 | 0.115 | 0.0042 | 1.195 | PTPN22 |
| 16 | rs12931878 | 10949695 | 362:446 | 0.812 | 0.0031 | | 0.16 | 0.225 | $1.01 \times 10^{-5}$ | 0.657 | 128:162 | 0.79 | 0.046 | $3.30 \times 10^{-7}$ | 0.158 | 0.178 | 0.0088 | 0.865 | KIAA0350 |
| 15 | rs8035957 | 36625556 | 423:342 | 1.24 | 0.0034 | | 0.304 | 0.263 | 0.011 | 1.225 | 204:162 | 1.259 | 0.028 | $1.00 \times 10^{-4}$ | 0.292 | 0.268 | 0.01 | 1.126 | RASGRP1* |
| 6 | rs3757247 | 91014184 | 545:482 | 1.13 | 0.049 | | 0.504 | 0.455 | 0.0075 | 1.216 | 253:209 | 1.211 | 0.041 | 0.001 | 0.511 | 0.489 | 0.033 | 1.092 | BACH2* |
| 1 | rs1983853 | 85083780 | 202:254 | 0.8 | 0.015 | | 0.121 | 0.151 | 0.021 | 0.779 | 105:136 | 0.772 | 0.046 | 0.001 | 0.122 | 0.137 | 0.036 | 0.878 | EDG7* |
| 11 | rs1004446 | 2126719 | 378:514 | 0.735 | $5.27 \times 10^{-6}$ | | 0.254 | 0.354 | $4.38 \times 10^{-9}$ | 0.622 | 160:228 | 0.7018 | $5.56 \times 10^{-4}$ | $1.02 \times 10^{-14}$ | 0.443 | 0.464 | 0.047 | 0.921 | INS |

Turning to the DCCT/EDIC cohort, signals in the genes encoding ubiquitin-associated and SH3 domain-containing protein A (UBASH3A) and BTB and CNC homology 2 (BACH2) replicated in this fifth independent cohort (Table 2) and the P-values were significant after correcting for the six tests carried out. Clearly the risks are relatively modest compared to previously described associations, and it is only when we had this sample size at our disposal could we detect and establish these signals as true positives through an independent replication; however, Table 3 shows that rs9976767 is in fact significant at the genome-wide level when all five cohorts utilized were combined i.e. $P=2.33\times 10^{-8}$.

TABLE 2

| Chr | SNP | Position | Gene | Aff allele freq | Ctrl allele freq | OR [95% CI] | P |
|---|---|---|---|---|---|---|---|
| 21 | rs9976767 | 42709459 | UBASH3A | 0.474 | 0.436 | 1.165 [1.051-1.292] | 0.0036 |
| 9 | rs10758593 | 4282083 | GLIS3 | 0.429 | 0.426 | 1.013 [0.913-1.124] | 0.81 |
| 9 | rs10758594 | 4285583 | GLIS3 | 0.434 | 0.443 | 0.963 [0.869-1.068] | 0.48 |
| 15 | rs8035957 | 36625556 | RASGRP1 | 0.270 | 0.261 | 1.047 [0.932-1.176] | 0.44 |
| 6 | rs3757247 | 91014184 | BACH2 | 0.497 | 0.463 | 1.144 [1.033-1.268] | 0.010 |
| 1 | rs1983853 | 85083780 | EDG7 | 0.132 | 0.153 | 0.842 [0.726-0.976] | 0.022 |

Replication results for the six SNPs of interest selected from the discovery process in the DCCT/EDIC T1D probands and CHOP controls. The two SNPs that successfully replicated are indicated in bold. Minor allele frequencies, P-values and odds ratios (OR) are shown, together with the gene in which the markers resides or which they are nearest to. P-values are two-sided in each instance. Aff allele freq, allele frequency in affected individuals; Chr, chromosome; CI, confidence interval; Ctrl allele freq, allele frequency in unaffected individuals.

The co-ordinates for the linkage disequilibrium (LD) block that harbor the signals provided in Table 2 are set forth below. The present invention encompasses any SNP with these blocks that associated with an increased risk of T1D.

TABLE 3

| GENE | CHR | B36 Start | B36 End |
|---|---|---|---|
| UBASH3A | 21 | 42689693 | 42725106 |
| GLIS3A | 9 | 4267839 | 4290501 |
| RASGRP1 | 15 | 36601669 | 36728371 |
| BACH2 | 6 | 90944672 | 91078212 |
| EDG7 | 1 | 85002281 | 85127151 |

See the world wide web at //genome.ucsc.edu/cgi-bin/hgGateway for the details relating to build 36 of the human genome which was assembled in March of 2006.

TABLE 4

Meta analysis of the five cohorts. Minor allele frequencies, P-values and odds ratios (OR) are shown, together with the relevant allele for each of the six SNPs.

| SNP | Allele | Gene | OR [95% CI] | P |
|---|---|---|---|---|
| rs9976767 | C | UBASH3A | 1.155 (1.098, 1.215) | $2.33 \times 10^{-8}$ |
| rs10758593 | A | GLIS3 | 1.131 (1.074, 1.190) | $2.64 \times 10^{-6}$ |
| rs10758594 | A | GLIS3 | 1.114 (1.058, 1.172) | $3.51 \times 10^{-5}$ |
| rs8035957 | C | RASGRP1 | 1.144 (1.080, 1.211) | $3.92 \times 10^{-6}$ |
| rs3757247 | A | BACH2 | 1.134 (1.078, 1.193) | $1.25 \times 10^{-6}$ |
| rs1983853 | A | EDG7 | 0.833 (0.773, 0.898) | $1.87 \times 10^{-6}$ |

UBASH3A is the only gene in this region of linkage disequilibrium. Mice lacking Sts2 (the mouse homologue for UBASH3A) have been shown to be normal in all respects, including T-cell function[23]. Mice lacking both Sts1 and Sts2 do have increased splenocyte numbers and are hyperresponsive to T-cell receptor stimulation. It has been suggested that STS1 and STS2 are critical regulators of the signaling pathways that regulate T-cell activation[23].

Figure 2:
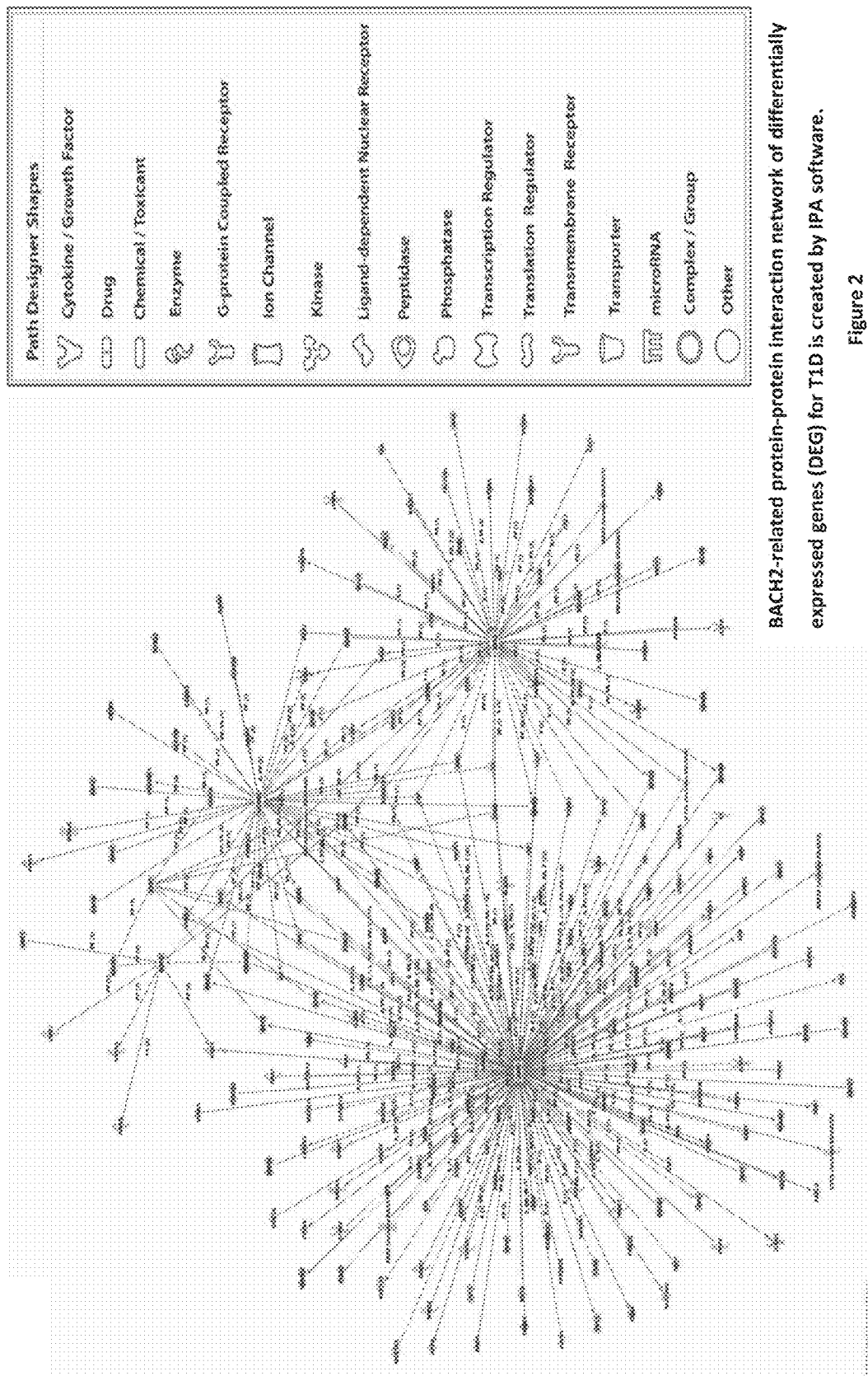
FIG. 2. BACH-2 related protein interaction network of differentially expressed genes for T1D.

BACH2 is also the only gene at this locus. The gene product is a member of the small Maf family which are basic region leucine zipper proteins that function either as transcriptional activators or repressors, depending on the proteins they heterodimerize with. Muto et al[24] found that Bach2-/- mice had relatively high levels of serum IgM but low levels of IgA and IgG subclasses. The Bach2-/- mice have also been reported to present with deficient T cell-independent and T cell-dependent IgG responses, leading the authors to conclude that BACH2 was a regulator of the antibody response[24]. Using IPA software, we generated a BACH-2 related protein-protein interaction network of differentially expressed genes (DEG) for T1D. Grey represents genes that are up regulated in T1D group versus controls. White represents gens that are down regulated in T1D. Solid lines show direct protein-protein interactions whereas dotted lines show indirect interactions. Different shapes represent different molecule types. See FIG. 2.

Figure 3:
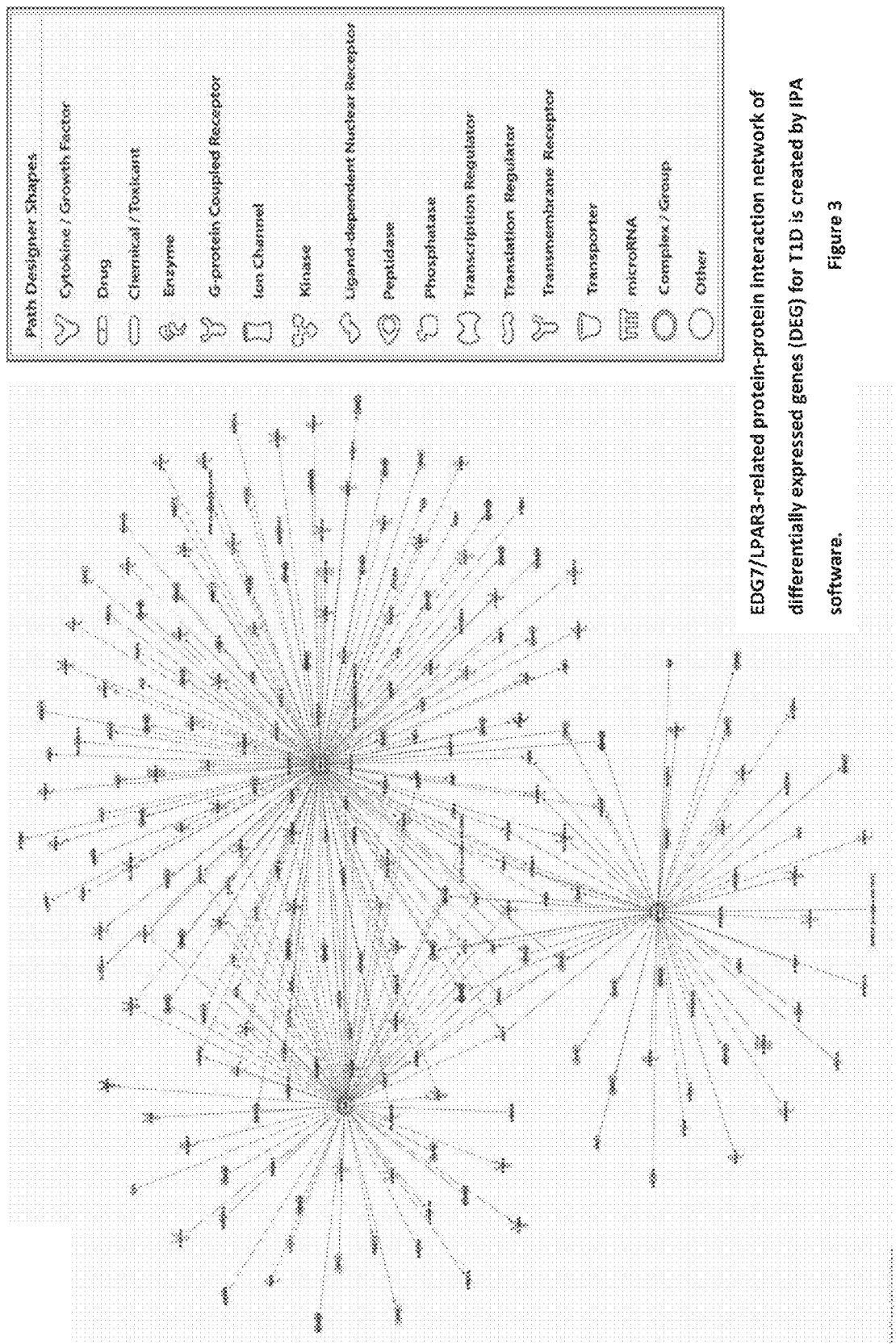
FIG. 3. EDG7/LPAR3 related protein interaction network of differentially expressed genes for T1D.

It should also be noted that rs1983853 yielded nominally significant association with T1D in all the cohorts but did not survive correction for multiple testing in the final replication attempt in the Toronto dataset. This SNP resides in endothelial differentiation gene 7 (EDG7; formerly LPA3), which has been implicated in mechanisms of embryo implantation[25]. Using IPA software, we generated an EDG7-LPAR3-related protein-protein interaction network of differentially expressed genes (DEG) for T1D. Grey represents genes that are up regulated in T1D group versus controls. White represents gens that are down regulated in T1D. Solid lines show direct protein-protein interactions whereas dotted lines show indirect interactions. Different shapes represent different molecule types. See FIG. 3.

REFERENCES

1. Todd, J. A., Bell, J. I. & McDevitt, H. O. HLA-DQ beta gene contributes to susceptibility and resistance to insulin-dependent diabetes mellitus. *Nature* 329, 599-604 (1987).
2. Risch, N. Assessing the role of HLA-linked and unlinked determinants of disease. *Am J Hum Genet* 40, 1-14 (1987).
3. Barratt, B. J. et al. Remapping the insulin gene/IDDM2 locus in type 1 diabetes. *Diabetes* 53, 1884-9 (2004).
4. Pugliese, A. et al. The insulin gene is transcribed in the human *thymus* and transcription levels correlated with allelic variation at the INS VNTR-IDDM2 susceptibility locus for type 1 diabetes. *Nat Genet* 15, 293-7 (1997).
5. Vafiadis, P. et al. Insulin expression in human *thymus* is modulated by INS VNTR alleles at the IDDM2 locus. *Nat Genet* 15, 289-92 (1997).
6. Bottini, N., Vang, T., Cucca, F. & Mustelin, T. Role of PTPN22 in type 1 diabetes and other autoimmune diseases. *Seminars in Immunology* 18, 207-213 (2006).

7. Vella, A. et al. Localization of a type 1 diabetes locus in the IL2RA/CD25 region by use of tag single-nucleotide polymorphisms. *Am J Hum Genet* 76, 773-9 (2005).
8. Qu, H. Q., Montpetit, A., Ge, B., Hudson, T. J. & Polychronakos, C. Toward further mapping of the association between the IL2RA locus and type 1 diabetes. *Diabetes* 56, 1174-6 (2007).
9. Lowe, C. E. et al. Large-scale genetic fine mapping and genotype-phenotype associations implicate polymorphism in the IL2RA region in type 1 diabetes. *Nat Genet* 39, 1074-1082 (2007).
10. Ueda, H. et al. Association of the T-cell regulatory gene CTLA4 with susceptibility to autoimmune disease. *Nature* 423, 506-11 (2003).
11. Hakonarson, H. et al. A genome-wide association study identifies KIAA0350 as a type 1 diabetes gene. *Nature* 448, 591-4 (2007).
12. Wellcome Trust Case Control Consortium. Genome-wide association study of 14,000 cases of seven common diseases and 3,000 shared controls. *Nature* 447, 661-678 (2007).
13. Todd, J. A. et al. Robust associations of four new chromosome regions from genome-wide analyses of type 1 diabetes. *Nat Genet* 39, 857-864 (2007).
14. Smyth, D. J. et al. A genome-wide association study of nonsynonymous SNPs identifies a type 1 diabetes locus in the interferon-induced helicase (IFIH1) region. *Nat Genet* 38, 617-619 (2006).
15. Hakonarson, H. et al. A genome-wide association study identifies KIAA0350 as a type 1 diabetes gene. *Nature* 448, 591-594 (2007).
16. Hakonarson, H. et al. A novel susceptibility locus for type 1 diabetes on Chr12q13 identified by a genome-wide association study. *Diabetes* 57, 1143-6 (2008).
17. Wellcome Trust Case Control Consortium. Genome-wide association study of 14,000 cases of seven common diseases and 3,000 shared controls. *Nature* 447, 661-78 (2007).
18. Todd, J. A. et al. Robust associations of four new chromosome regions from genome-wide analyses of type 1 diabetes. *Nat Genet* 39, 857-64 (2007).
19. The Diabetes Control and Complications Trial Research Group. The effect of intensive treatment of diabetes on the development and progression of long-term complications in insulin-dependent diabetes mellitus. The Diabetes Control and Complications Trial Research Group. *N Engl J Med* 329, 977-86 (1993).
20. The Diabetes Control and Complications Trial (DCCT). The Diabetes Control and Complications Trial (DCCT). Design and methodologic considerations for the feasibility phase. The DCCT Research Group. *Diabetes* 35, 530-45 (1986).
21. Price, A. L. et al. Principal components analysis corrects for stratification in genome-wide association studies. *Nat Genet* 38, 904-9 (2006).
22. Purcell, S. et al. PLINK: a tool set for whole-genome association and population-based linkage analyses. *Am J Hum Genet* 81, 559-75 (2007).
23. Carpino, N. et al. Regulation of ZAP-70 activation and TCR signaling by two related proteins, Sts-1 and Sts-2. *Immunity* 20, 37-46 (2004).
24. Muto, A. et al. Identification of Bach2 as a B-cell-specific partner for small maf proteins that negatively regulate the immunoglobulin heavy chain gene 3' enhancer. *Embo J* 17, 5734-43 (1998).
25. Ye, X. et al. LPA3-mediated lysophosphatidic acid signaling in embryo implantation and spacing. *Nature* 435, 104-8 (2005).

Example II

The RASGRP1 Locus and T1D

As described above, we had previously identified a SNP, rs8035957, in the RASGRP1 locus that was associated with T1D. The two genome-wide association studies published by us and by the Wellcome Trust Case-Control Consortium (WTCCC) revealed a number of novel loci.

In additional studies, we analyzed data from two sources: 1) The previously published second stage of our study, with a total sample size of the two stages consisting of 1,046 Canadian case-parent trios and 538 multiplex families with 929 affected offspring from the Type 1 Diabetes Genetics Consortium (T1DGC); 2) The RR2 project of the T1DGC, which genotyped 4,417 individuals from 1,062 non-overlapping families, including 2,059 affected individuals (mostly sibling pairs) for the 1,536 markers with the highest statistical significance for type 1 diabetes in the WTCCC results.

One locus, mapping to an LD block at chr15q14, reached statistical significance by combining results from two markers (rs17574546 and rs7171171) in perfect linkage disequilibrium (LD) with each other ($r^2=1$). We obtained a joint p value of $1.3\times10^{-6}$, which exceeds by an order of magnitude the conservative threshold of $3.26\times10^{-5}$ obtained by correcting for the 1,536 SNPs tested in our study. Meta-analysis with the original WTCCC genome-wide data produced a p value of $5.83\times10^{-9}$.

These studies confirm that the results presented in Example 1 identifying a novel type 1 diabetes locus involving the RASGRP1 gene. This gene is known to play a crucial role in thymocyte differentiation and TCR signaling by activating the Ras signaling pathway.

The following materials and methods are similar to those described in Example I and are provided to facilitate the practice of Example 2.

1. The T1DGC RR2 study genotyped 4,417 individuals from 1,062 type 1 diabetes families, including 2,059 affected siblings and both their parents for the 1,536 markers with the highest statistical significance for type 1 diabetes in the WTCCC results. Genotyping was performed at the Sanger Institute on the Illumina Golden Gate platform. Most subjects were of European ancestry, with a median age at onset of 10 years (lower and upper quartiles at 6 years and 15.5 years).

2. In our study, we genotyped 1,046 type 1 diabetes type 1 diabetes case-parent trios, collected in pediatric diabetes clinics in Montreal, Toronto, Ottawa and Winnipeg. The median age at onset is 8.4 years with lower and upper quartiles at 5.0 years and 11.8 years. Ethnic backgrounds were of mixed European descent, with the largest single subset (40%) being French Canadian. The Research Ethics Board of the Montreal Children's Hospital and other participating centers approved the study, and written informed consent was obtained from all subjects. In addition, we genotyped 549 families with at least one child with type 1 diabetes and both parents (946 total affected). The median age at onset is 8 with quartiles at 4 years and 13 years. The samples were collected in Europe, North America and Australia and most subjects were of European ancestry. Genotyping data from 11 overlapping families that were also included in the RR2 study were removed for analysis. As we previously described[4], we used the Illumina Golden Gate array to genotype 982 markers with p<0.05 in both the TDT and case-control phase of our original GWAS. In addition, 15 single-nucleotide polymorphisms (SNP) with p<0.1 in each of our two GWA cohorts and p<0.01 in WTCCC were genotyped using mass spectrometry on the Sequenom iPlex platform.

3. Statistics

Type 1 diabetes association was tested by the Family Based Association Test (FBAT) software available on the world wide web at biostat.harvard.edu/~fbat/fbat.htm[8]. Considering most of the T1DGC families have multiple siblings, the option of the empirical variance was used in the FBAT statistics to permit a robust but unbiased test of genetic association. As 1,536 SNPs were tested in the RR2 study, we used a conserved significance threshold corrected for multiple comparisons at $3.26 \times 10^{-5}$.

Results

Recently, two independent studies validated the type 1 diabetes association of UBASH3A and BACH2[2,3]. Further research confirms that the RASGRP1 locus is also an important type 1 diabetes locus. Overlap in the markers selected in the two projects was determined either by identity of SNPs or, in cases of physical proximity (<1 Mb), by LD ($r^2$ value>0.8). After excluding known type 1 diabetes loci, there was only one locus nominally significant (P<0.05) in both projects. It involves a locus evaluated in the RR2 cohort by SNP rs17574546 ($P=3.41 \times 10^{-3}$) and in our set by rs7171171 ($P=8.40 \times 10^{-5}$, Table 5).

TABLE 5

Association analysis between the RASGRP1 variations and type 1 diabetes

| Cohort | Minor allele (Frequency) | Hardy-Weinberg p | Informative family number* | Z (P value) |
|---|---|---|---|---|
| The T1DGC RR2 cohort | | | | |
| rs17574546 | C (0.225) | 0.931 | 302 | 2.93 ($P = 3.41 \times 10^{-3}$) |
| The Canadian cohort and extra T1DGC samples[†] | | | | |
| rs7171171 | G (0.207) | 0.873 | 665 | 3.93 ($P = 8.40 \times 10^{-5}$) |
| Combined analysis | — (0.209) | 1.000 | 967 | 4.84 ($P = 1.30 \times 10^{-6}$) |

*Number of families informative for (with a non-zero contribution to) the FBAT analysis;
[†]No redundant sample with the T1DGC RR2 cohort.

The genotype calling rate of rs17574546 in the RR2 samples is 99.8%, and for rs7171171 in our own samples is 99.9%. No Mendelian error was found in either. As these SNPs are in perfect LD ($r^2=1$) we performed a direct combined analysis which showed $P=1.30 \times 10^{-6}$. This exceeds by more than an order of magnitude the corrected significance level. The OR (95% CI) estimated on the combined family dataset is 1.22 (1.12, 1.33), while the OR (95% CI) in the WTCCC case-control set is 1.21 (1.09, 1.33) ($P=2.67 \times 10^{-4}$). The meta-analysis of these two results gives an OR (95% CI)=1.21 (1.14, 1.30) and $P=5.83 \times 10^{-9}$, a significance level accepted for genome-wide studies. Based on these results, we can conclude that the RASGRP1 locus is associated with type 1 diabetes. It is interesting to note that rs17574546 and rs7171171 both have D'=0.902, and $r^2=0.553$, with rs8035957 described in Example 1.

This novel type 1 diabetes association signal maps to a LD block at Chr15q14, ~13 kb upstream of the transcription start site of the RASGRP1 gene, and has no LD with any known type 1 diabetes locus. See FIG. 1. As type 1 diabetes is caused by the autoimmune destruction of pancreatic β-cells, it is interesting that the RASGRP1 gene has an important immune function. RASGRP1 (NCBI GeneID: 10125) encodes calcium and DAG-regulated RAS guanyl releasing protein 1 (RasGRP1)[9]. RasGRP1 plays crucial roles in thymocyte differentiation and TCR signaling by activating the Ras signaling pathway. RasGRP1-null mutant mice have approximately normal numbers of immature thymocytes but a marked deficiency of mature, single-positive (CD4$^+$CD8$^-$ and CD4$^-$CD8$^+$) thymocytes[10]. Transgenic expression of RasGRP1 induces the maturation of double-negative thymocytes and enhances the production of CD4$^-$CD8$^+$ thymocytes[11]. In addition, RasGRP1 has dramatic effect on the development and function of CD4$^+$CD25$^+$ regulatory T-cells ($T_{reg}$). In the absence of RasGRP1, the development of CD4$^+$CD25$^+$T$_{reg}$ in the *thymus* is severely impaired, whereas the peripheral expansion and function of CD4$^+$CD25$^+$T$_{reg}$ are greatly increased[12]. CD4$^+$CD25$^+$ T$_{reg}$ plays a critical role in maintaining immune homeostasis and inhibiting autoimmune reaction of type 1 diabetes and other autoimmune diseases[13]. As the transfer of CD4$^+$CD25$^+$ CD4$^+$CD25$^+$ T$_{reg}$ cells can prevent type 1 diabetes in the recipient NOD mice[14], knowledge of the role of genes involved in the generation of this subset in type 1 diabetes may play an important role in the development of preventive interventions.

REFERENCES

1. Hakonarson H, Grant S F, Bradfield J P, Marchand L, Kim C E, Glessner J T, Grabs R, Casalunovo T, Taback S P, Frackelton E C, Lawson M L, Robinson L J, Skraban R, Lu Y, Chiavacci R M, Stanley C A, Kirsch S E, Rappaport E F, Orange J S, Monos D S, Devoto M, Qu H Q, Polychronakos C. A genome-wide association study identifies KIAA0350 as a type 1 diabetes gene. *Nature* 2007; 448:591-4.
2. Wellcome Trust Case Control Consortium. Genome-wide association study of 14,000 cases of seven common diseases and 3,000 shared controls. *Nature* 2007; 447: 661-678.
3. Todd J A, Walker N M, Cooper J D, Smyth D J, Downes K, Plagnol V, Bailey R, Nejentsev S, Field S F, Payne F, Lowe C E, Szeszko J S, Hafler J P, Zeitels L, Yang J H M, Vella A, Nutland S, Stevens H E, Schuilenburg H, Coleman G, Maisuria M, Meadows W, Smink L J, Healy B, Burren O S, Lam A A C, Ovington N R, Allen J, Adlem E, Leung H-T, Wallace C, Howson J M M, Guja C, Ionescu-Tirgoviste C, Simmonds M J, Heward J M, Gough S C L, Dunger D B, Wicker L S, Clayton D G. Robust associations of four new chromosome regions from genome-wide analyses of type 1 diabetes. *Nat Genet* 2007; 39:857-864.
4. Grant S F, Qu H Q, Bradfield J P, Marchand L, Kim C E, Glessner J T, Grabs R, Taback S P, Frackelton E C, Eckert A W, Annaiah K, Lawson M L, Otieno F G, Santa E, Shaner J L, Smith R M, Skraban R, Imielinski M, Chiavacci R M, Grundmeier R W, Stanley C A, Kirsch S E, Waggott D, Paterson A D, Monos D S, Polychronakos C, Hakonarson H. Follow-up analysis of genome-wide association data identifies novel loci for type 1 diabetes. *Diabetes* 2009; 58:290-5.

5. Cooper J D, Smyth D J, Smiles A M, Plagnol V, Walker N M, Allen J E, Downes K, Barrett J C, Healy B C, Mychaleckyj J C, Warram J H, Todd J A. Meta-analysis of genome-wide association study data identifies additional type 1 diabetes risk loci. *Nat Genet* 2008; 40:1399-401.
6. Concannon P, Onengut-Gumuscu S, Todd J A, Smyth D J, Pociot F, Bergholdt R, Akolkar B, Erlich H A, Hilner J E, Julier C, Morahan G, Nerup J, Nierras C R, Chen W M, Rich S S. A human type 1 diabetes susceptibility locus maps to chromosome 21q22.3. *Diabetes* 2008; 57:2858-61.
7. Rich S S, Concannon P, Erlich H, Julier C, Morahan G, Nerup J, Pociot F, Todd J A. The Type 1 Diabetes Genetics Consortium. *Ann N Y Acad Sci* 2006; 1079:1-8.
8. Horvath S, Xu X, Laird N M. The family based association test method: strategies for studying general genotype—phenotype associations. *Eur J Hum Genet* 2001; 9:301-6.
9. Ebinu J O, Bottorff D A, Chan E Y, Stang S L, Dunn R J, Stone J C. RasGRP, a Ras guanyl nucleotide-releasing protein with calcium- and diacylglycerol-binding motifs. *Science* 1998; 280:1082-6.
10. Dower N A, Stang S L, Bottorff D A, Ebinu J O, Dickie P, Ostergaard H L, Stone J C. RasGRP is essential for mouse thymocyte differentiation and TCR signaling. *Nature Immunology* 2000; 1:317-321.
11. Norment A M, Bogatzki L Y, Klinger M, Ojala E W, Bevan M J, Kay R J. Transgenic expression of RasGRP1 induces the maturation of double-negative thymocytes and enhances the production of CD8 single-positive thymocytes. *J Immunol* 2003; 170:1141-9.
12. Chen X, Priatel J J, Chow M T, Teh H-S. Preferential Development of CD4 and CD8 T Regulatory Cells in RasGRP1-Deficient Mice. *J Immunol* 2008; 180:5973-5982.
13. Shevach E M. Certified professionals: CD4(+)CD25(+) suppressor T cells. *J Exp Med* 2001; 193:F41-6.
14. Salomon B, Lenschow D J, Rhee L, Ashourian N, Singh B, Sharpe A, Bluestone J A. B7/CD28 Costimulation Is Essential for the Homeostasis of the CD4+CD25+ Immunoregulatory T Cells that Control Autoimmune Diabetes. *Immunity* 2000; 12:431.

Example III

Diagnostic Methods for T1D and Screening Assays to Identify Therapeutic Agents Useful for the Treatment of T1D The information herein above can be applied clinically to patients for diagnosing an increased susceptibility for developing T1D, and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing T1D. This can occur after a patient arrives in the clinic; the patient has blood drawn, and using the diagnostic methods described herein, a clinician can detect a SNP in the regions of chromosome 21, 15, 6, 9 and 1 described herein. The typical age range for a patient to be screened is between 9 and 12 years of age. The information obtained from the patient sample, which can optionally be amplified prior to assessment, will be used to diagnose a patient with an increased or decreased susceptibility for developing T1D. Kits for performing the diagnostic method of the invention are also provided herein. Such kits comprise a microarray comprising at least one of the SNPs provided herein in and the necessary reagents for assessing the patient samples as described above.

The identity of T1D-involved genes and the patient results will indicate which variants are present, and will identify those that possess an altered risk for developing T1D. The information provided herein allows for therapeutic intervention at earlier times in disease progression that previously possible. Also as described herein above, UBASH3A, GLIS3, RASGRP1, BACH2, and EDG7 provide novel targets for the development of new therapeutic agents efficacious for the treatment of T1D. In particular, it would be desirable to block expression of these genes in those patients that are more prone to develop the disease. In this regard, the therapeutic siRNAs described herein can be used to block expression of the gene product based on the patient signal, thereby inhibiting the pancreatic β-cell destruction that occurs in T1D.

Candidate siRNA compositions for use in the invention are provided in Tables 6-10. The sequences in Tables 6-10 include several siRNAs (i.e., sense sequences for a target region). Those of skill in the art can determine the sequence of an antisense siRNA strand based on the disclosure of the sense strand, and will appreciate the difference between any "U" and "T" designations in the sequences which correspond to RNA and DNA molecules, respectively. Also, methods of using known inhibitors of UBASH3A, GLIS3, RASGRP1, BACH2 and EDG7 to treat T1D are also provided. See the tables below. In addition, shRNA constructs can be designed based on the sense sequence provided in Tables 4-8, and may be effective to inhibit UBASH3A, GLIS3, RASGRP1, BACH2 and EDG7. The shRNA constructs utilizing the sense strand from Tables 6-10 for the respective targets would include a hairpin loop 3' to the sense sequence (e.g., suitable hairpins include, but are not limited to: TCAAGAG, TTCAAGAGA, GAAGCTTG, and TTCG) followed by the corresponding antisense sequence from the sense strand provided in Tables 6-10. Table 10B provides known small molecule antagonists of EDG7 which should have utility for the treatment of T1D.

TABLE 6

| Candidate UBASH3 siRNA molecules (sense) | |
|---|---|
| GCATTTAACTGGAGGAACTtt | SEQ ID NO: 6 |
| CAAGAGTTCTGGAGAGAGAtt | SEQ ID NO: 7 |
| GAACAGAGCTCATGAGGTCtt | SEQ ID NO: 8 |
| AATCAAGATACGAGTGGAAtt | SEQ ID NO: 9 |
| GGATCGAGCCAGTGAGTCTtt | SEQ ID NO: 10 |
| CGGCGAGCATGGTGCAAATtt | SEQ ID NO: 11 |
| GGAACTGGATCTCAGGCAAtt | SEQ ID NO: 12 |
| GTGGATGAGCTGACGCTAAtt | SEQ ID NO: 13 |
| GAAAATGGGAGTTGGTGAAtt | SEQ ID NO: 14 |
| ACGCCAAGGTCTCCAACAAtt | SEQ ID NO: 15 |
| GGACATGGCCCTAACCTGAtt | SEQ ID NO: 16 |
| GGGAGAGAGTGGATCAGATtt | SEQ ID NO: 17 |
| CCAAACTCATCCTGGAAGAtt | SEQ ID NO: 18 |

TABLE 6-continued

Candidate UBASH3 siRNA molecules (sense)

| Sequence | SEQ ID |
|---|---|
| GAGTCTGACACGTGGGTGAtt | SEQ ID NO: 19 |
| GGAGAGAGAGCAAGCGCCAtt | SEQ ID NO: 20 |
| GAAGAGAGCTGGAGACAGGtt | SEQ ID NO: 21 |
| GGGAATTCGCCATGACCTTtt | SEQ ID NO: 22 |
| GGCCCTAACCTGAGGCTGAtt | SEQ ID NO: 23 |
| CGTGAAGCCTTGCACCAAAtt | SEQ ID NO: 24 |
| GGAAAATGGGAGTTGGTGAtt | SEQ ID NO: 25 |
| GGGCGAACGCAGCATTTAAtt | SEQ ID NO: 26 |
| AGTTCTGGAGAGAGCAAtt | SEQ ID NO: 27 |
| GTGAAGACCAGAAGGTGGAtt | SEQ ID NO: 28 |
| AGGCTGAGCAATTTAACTAtt | SEQ ID NO: 29 |
| CAGCAGATGCAGCGGGGAAtt | SEQ ID NO: 30 |
| GGACAGTGGTATCAGAATCtt | SEQ ID NO: 31 |
| AGACGCAGCTCTACGCCAAtt | SEQ ID NO: 32 |
| AGGCATGGCTGCAGCAATGtt | SEQ ID NO: 33 |
| TGGAAGAACTCAAACTGGAtt | SEQ ID NO: 34 |
| CTGAAGAGAGCTGGAGACAtt | SEQ ID NO: 35 |
| AACCTGAGGCTGAGCAATTtt | SEQ ID NO: 36 |
| GCACCAAACAGCTGCATCTtt | SEQ ID NO: 37 |
| GCACTCTACTCCCGAGACAtt | SEQ ID NO: 38 |
| GGGTGAAGCACAGGATGTAtt | SEQ ID NO: 39 |
| CCACAAACGGCAAGGAGTCtt | SEQ ID NO: 40 |
| CAAACGGCAAGGAGTCTTAtt | SEQ ID NO: 41 |
| GGTGAAGCCAGCAGCAGATtt | SEQ ID NO: 42 |
| CAAAATGGGAAGCTGGCAAtt | SEQ ID NO: 43 |
| GCCTGGAAGAGCTGAAAGAtt | SEQ ID NO: 44 |
| AAGAGCTGAAAGAGGCAAAtt | SEQ ID NO: 45 |
| CGGTGAAGACCCTGACCCAtt | SEQ ID NO: 46 |
| GAGCCCTATTCCAGTACAAtt | SEQ ID NO: 47 |
| GCAAGGAGTCTTAGCAGCTtt | SEQ ID NO: 48 |
| CCATTATCATCGTGTGGCAtt | SEQ ID NO: 49 |
| GGAAGAGCTGAAAGAGGCAtt | SEQ ID NO: 50 |
| CAACATTGACACTGATTACtt | SEQ ID NO: 51 |
| GAAAATAAAGAGGAAGGAAtt | SEQ ID NO: 52 |
| CTTCAAGAGTTCTGGAGAGtt | SEQ ID NO: 53 |
| CCGGAAAACTACACGGATCtt | SEQ ID NO: 54 |
| GTGAAGCACAGGATGTACAtt | SEQ ID NO: 55 |

TABLE 7

Candidate GLIS3 siRNA molecules (sense)

| Sequence | SEQ ID |
|---|---|
| GCACAGAGCTCCATCCAGAtt | SEQ ID NO: 56 |
| GCTATAAACTGCTGATCCAtt | SEQ ID NO: 57 |
| TCACATACTTTAAAGCCAAtt | SEQ ID NO: 58 |
| GGGCAGCACCGTAGACCTAtt | SEQ ID NO: 59 |
| GGTCAGTGGTCATCACATTtt | SEQ ID NO: 60 |
| ACGCAGGAGCTGAGAGGTTtt | SEQ ID NO: 61 |
| CCTATCAGCCAGAAACAAAtt | SEQ ID NO: 62 |
| TCAGAATGGCCTTGATCTAtt | SEQ ID NO: 63 |
| GGAAAAGGCAGCTGCAACAtt | SEQ ID NO: 64 |
| GGGCAATGAATGCAGCCAAtt | SEQ ID NO: 65 |
| AGGAGTGGTCCCAGGGCTAtt | SEQ ID NO: 66 |
| CCGAACGCCTGGAGGAGTTtt | SEQ ID NO: 67 |
| GAGCAACAAGCAAGGAAAAtt | SEQ ID NO: 68 |
| GGAGACAAATGCTCACCAAtt | SEQ ID NO: 69 |
| CCAGATCAGTCCTAGCTTAtt | SEQ ID NO: 70 |
| GAATATACCTCCTTCAGATtt | SEQ ID NO: 71 |
| GTTTGAAGGTTGCGAGAAGtt | SEQ ID NO: 72 |
| GGACGCATCTGGACACCAAtt | SEQ ID NO: 73 |
| AGAGCAACAAGCAAGGAAAtt | SEQ ID NO: 74 |
| AGCCAAAGCAGCAGGAGTTtt | SEQ ID NO: 75 |
| GCTTTGGGCCTCAGTGCAAtt | SEQ ID NO: 76 |
| TATTCAAGCCGAAGTGGAAtt | SEQ ID NO: 77 |
| CTTCAATACTGCAAAGAACtt | SEQ ID NO: 78 |
| CTAACAACCTCCATCTCAAtt | SEQ ID NO: 79 |
| GCAACAATCTAGTGGTCACtt | SEQ ID NO: 80 |
| CCTCAAGCATGAAGCAGGAtt | SEQ ID NO: 81 |
| GGATGGCTCCTCAGAACAAtt | SEQ ID NO: 82 |
| ACCTTGAGTCTGACGAAAtt | SEQ ID NO: 83 |
| GTACCAAACGCTACACAGAtt | SEQ ID NO: 84 |
| CTGTCTACACCGAAGGCTAtt | SEQ ID NO: 85 |
| TGTCTACACCGAAGGCTAAtt | SEQ ID NO: 86 |
| GCATGAAGCAGGAGTGGTCtt | SEQ ID NO: 87 |
| CCAAAGAGCAACAAGCAAGtt | SEQ ID NO: 88 |
| TAGAGATGCTGCTGCTGAAtt | SEQ ID NO: 89 |
| AGCAATTATTCAAGCCGAAtt | SEQ ID NO: 90 |
| TCAGATACCAGGTCCCTTAtt | SEQ ID NO: 91 |
| CCTAGCTTACAGAGGGCAAtt | SEQ ID NO: 92 |
| TTGTCAAATTCCAGGATGTtt | SEQ ID NO: 93 |
| ACCCAAGTTCCCTAAGAAAtt | SEQ ID NO: 94 |

TABLE 7-continued

Candidate GLIS3 siRNA molecules (sense)

| | |
|---|---|
| CCTAAGAAAGCATGTGAAGtt | SEQ ID NO: 95 |
| TCCTCCAAATCCTGGGAAAtt | SEQ ID NO: 96 |
| CCTTATTTCGCGTGAGTCTtt | SEQ ID NO: 97 |
| CAGTCGGCCTCAAGCATGAtt | SEQ ID NO: 98 |
| ACACAGGCGAGAAGCCGTAtt | SEQ ID NO: 99 |
| CACCAAACCTTATGCTTGTtt | SEQ ID NO: 100 |
| ACCTTATGCTTGTCAAATTtt | SEQ ID NO: 101 |
| CAGCAATTATTCAAGCCGAtt | SEQ ID NO: 102 |
| CCACAGAGCCTTCTCGACTtt | SEQ ID NO: 103 |
| CCAATGGGAAGCCGCGATTtt | SEQ ID NO: 104 |
| GGAAAGGGGCTCTTGGCTTtt | SEQ ID NO: 105 |

TABLE 8

Candidate RASGRP1 siRNA molecules (sense)

| | |
|---|---|
| AAGCAAGACTAGAGGCAAAtt | SEQ ID NO: 106 |
| GAAACTTACTCAAAGGATAtt | SEQ ID NO: 107 |
| CCAGAAACTACGACAATTAtt | SEQ ID NO: 108 |
| TGAAATATGCACAGAAGAAtt | SEQ ID NO: 109 |
| CCACAGAGCTCCACCACTAtt | SEQ ID NO: 110 |
| GGAAAGTGAACGTCCATAAtt | SEQ ID NO: 111 |
| GCAAACGTCCAGAGGATtt | SEQ ID NO: 112 |
| GGATGAAATCTATGAGCTTtt | SEQ ID NO: 113 |
| CCTAAAGATCCAACTGAAAtt | SEQ ID NO: 114 |
| ACAAGGATATCGATGTAAAtt | SEQ ID NO: 115 |
| GGATATCGTTCTCTGATTAtt | SEQ ID NO: 116 |
| AAACAAGGATATCGATGTAtt | SEQ ID NO: 117 |
| TGGTTGTGTTTGAGTGTAAtt | SEQ ID NO: 118 |
| TGGTGAAAGCTAAGGGTGAtt | SEQ ID NO: 119 |
| GCAAAGATCTGGTTGTGTTtt | SEQ ID NO: 120 |
| TTGTCAAGTGGGAGAATAAtt | SEQ ID NO: 121 |
| GCACAGAAGAAAATAGAATtt | SEQ ID NO: 122 |
| TCAATAAGGTTCTCGGTGAtt | SEQ ID NO: 123 |
| CGACCAGGATGGATACATTtt | SEQ ID NO: 124 |
| CGGGATGAACTGTCACAAAtt | SEQ ID NO: 125 |
| GCCCAGTCTTGGTCAGAAAtt | SEQ ID NO: 126 |
| AGGAACTGGTGAAAGCTAAtt | SEQ ID NO: 127 |
| GCTCCATGCACCTGAGGAAtt | SEQ ID NO: 128 |
| GAATAAAGACTCCCTCATAtt | SEQ ID NO: 129 |
| AGGTATTGGATAACAGAATtt | SEQ ID NO: 130 |

TABLE 8-continued

Candidate RASGRP1 siRNA molecules (sense)

| | |
|---|---|
| AAGCTAAGGGTGAGGAGTTtt | SEQ ID NO: 131 |
| ACACTGAGGATGAAATCTAtt | SEQ ID NO: 132 |
| TGACAACTGTGCTGGATTTtt | SEQ ID NO: 133 |
| GGATATCGATGTAAAGACTtt | SEQ ID NO: 134 |
| AATAAAGACTCCCTCATAAtt | SEQ ID NO: 135 |
| GATGGAAACCTGTGTCGAAtt | SEQ ID NO: 136 |
| GAGAGAGGCTCCGCGGAAAtt | SEQ ID NO: 137 |
| GGGTACAACTGATGGTTCTtt | SEQ ID NO: 138 |
| GGGATGAGATCACAGCCTAtt | SEQ ID NO: 139 |
| GTAAGAAGCGAGCCAAGAAtt | SEQ ID NO: 140 |
| ATAAAGACTCCCTCATAAAtt | SEQ ID NO: 141 |
| GAAATATGCACAGAAGAAAtt | SEQ ID NO: 142 |
| GGAAACCTGTGTCGAAGTAtt | SEQ ID NO: 143 |
| GGTATTGGATAACAGAATTtt | SEQ ID NO: 144 |
| AGCTAAGGGTGAGGAGTTAtt | SEQ ID NO: 145 |
| TGACACAACTCAAATCAATtt | SEQ ID NO: 146 |
| CAGAAGAGCTATCCGAGCAtt | SEQ ID NO: 147 |
| CCTTCTGTGTGATGGACAAtt | SEQ ID NO: 148 |
| CCTCACAACTTCCAAGAGAtt | SEQ ID NO: 149 |
| GAGTGATCAAACAAGGATAtt | SEQ ID NO: 150 |
| GATCAAACAAGGATATCGAtt | SEQ ID NO: 151 |
| AGGAAGACAGCCCAGGATAtt | SEQ ID NO: 152 |
| CCAAGAACTGGAACAGGAAtt | SEQ ID NO: 153 |
| AAGAACTGGAACAGGAAATtt | SEQ ID NO: 154 |
| CCCTAAAGATCCAACTGAAtt | SEQ ID NO: 155 |

TABLE 9

Candidate BACH2 siRNA molecules (sense)

| | |
|---|---|
| GAAGATAACTCTAGCAACAtt | SEQ ID NO: 156 |
| GTGAAGAGAATGAGGAAGAtt | SEQ ID NO: 157 |
| CAAATTGGTGTGTGAGAAAtt | SEQ ID NO: 158 |
| CAGGAGAGGAGGAGGATGAtt | SEQ ID NO: 159 |
| AGAATGAGGAAGAGAGCATtt | SEQ ID NO: 160 |
| CAGAACAGTTAGAGTTTATtt | SEQ ID NO: 161 |
| GGAAATGACTGATAAGTGTtt | SEQ ID NO: 162 |
| CTTTGATCGTGGAGAGGAAtt | SEQ ID NO: 163 |
| GAGAGGAGGAGGATGAAGAtt | SEQ ID NO: 164 |
| GTACCAAGAATGTCTATAAtt | SEQ ID NO: 165 |

TABLE 9-continued

Candidate BACH2 siRNA molecules (sense)

| | |
|---|---|
| GAGATGAGCCTGACGCCAAtt | SEQ ID NO: 167 |
| GAGAAACTGTTGTCAGAGAtt | SEQ ID NO: 168 |
| AGAGAGGAATCAACTGAAAtt | SEQ ID NO: 169 |
| CAGTGAAGAGAATGAGGAAtt | SEQ ID NO: 170 |
| GGTGTGTGAGAAAGAGAAAtt | SEQ ID NO: 171 |
| GAGGAGGAGACGATGGATTtt | SEQ ID NO: 172 |
| GGGAAGATAACTCTAGCAAtt | SEQ ID NO: 173 |
| AAAGGAAACTGGACTGTATtt | SEQ ID NO: 174 |
| GCAAATTGGTGTGTGAGAAtt | SEQ ID NO: 175 |
| AAGAGAAACTGTTGTCAGAtt | SEQ ID NO: 176 |
| ATGAAGAGGAGGAGACGATtt | SEQ ID NO: 177 |
| GGTTGGAGGCTCTCTGTAAtt | SEQ ID NO: 178 |
| CAGCAACACCTCCGAGAATtt | SEQ ID NO: 179 |
| AAACAGTGACCGTGGACTTtt | SEQ ID NO: 180 |
| GAACAGCCCAGGAAAGATTtt | SEQ ID NO: 181 |
| CCTCAGAACAGTTAGAGTTtt | SEQ ID NO: 182 |
| GTGCTGAGTTCCTGCGCATtt | SEQ ID NO: 183 |
| GCGAGAACTCTGCAGGAGAtt | SEQ ID NO: 184 |
| CTGCAGGAGAGGAGGAGGAtt | SEQ ID NO: 185 |
| CCGTAGCAGAGAAGGAAGAtt | SEQ ID NO: 186 |
| GCCAGAAGGAGGTGTCCAAtt | SEQ ID NO: 187 |
| GGGTGAGCAGTTTGGACAAtt | SEQ ID NO: 188 |
| CCAGGAAAGATTATACCTAtt | SEQ ID NO: 189 |
| CCTCAATGACCAGCGGAAAtt | SEQ ID NO: 190 |
| CTGTTACTCAGCAGAGAAAtt | SEQ ID NO: 191 |
| GCCAGGAAATGACTGATAAtt | SEQ ID NO: 192 |
| AGAAGGAGGTGTCCAACTTtt | SEQ ID NO: 193 |
| CCAAATTAAATGTGAGCAGtt | SEQ ID NO: 194 |
| AGGAATCAACTGAAAGCATtt | SEQ ID NO: 195 |
| CAGGAAGTTTGCCGAGACAtt | SEQ ID NO: 196 |
| AGGAGGAGGATGAAGAGGAtt | SEQ ID NO: 197 |
| AGGAGGATGAAGAGGAGGAtt | SEQ ID NO: 198 |
| ACCAAGGAGAGCTCAGAAAtt | SEQ ID NO: 199 |
| TCACAGGGAATTATGGACAtt | SEQ ID NO: 200 |
| GTTGGAGGCTCTCTGTAAAtt | SEQ ID NO: 201 |
| GAGACCAGGACCAGGACTTtt | SEQ ID NO: 202 |
| CCACAGAACATCAGGAACCtt | SEQ ID NO: 203 |
| TTAAATGTGAGCAGTCTTAtt | SEQ ID NO: 204 |
| TCTCGGAAGCAGACAGTGAtt | SEQ ID NO: 205 |

TABLE 9-continued

Candidate BACH2 siRNA molecules (sense)

| | |
|---|---|
| CTTGAACCCAGGAGCCAAtt | SEQ ID NO: 206 |

TABLE 10A

Candidate EDG7 siRNA molecules (sense)

| | |
|---|---|
| CCTACAAGGACGAGGACATtt | SEQ ID NO: 207 |
| TCTACTACCTGTTGGCTAAtt | SEQ ID NO: 208 |
| TCATCATGGTTGTGGTGTAtt | SEQ ID NO: 209 |
| GTACATAGAGGATAGTATTtt | SEQ ID NO: 210 |
| GTCGATGACTGGACAGGAAtt | SEQ ID NO: 211 |
| GTGGAGAGGCACATGTCAAtt | SEQ ID NO: 212 |
| GGATGCGGGTCCATAGCAAtt | SEQ ID NO: 213 |
| CCATGAAGCTAATGAAGACtt | SEQ ID NO: 214 |
| AATAGGAGCAACACTGATAtt | SEQ ID NO: 215 |
| AGTACATAGAGGATAGTATtt | SEQ ID NO: 216 |
| CAATAAAAGCACTTCCTAAtt | SEQ ID NO: 217 |
| ATGACAAGCACATGGACTTtt | SEQ ID NO: 218 |
| GTGTACGTCAAGAGGAAAAtt | SEQ ID NO: 219 |
| AAGCTAATGAAGACGGTGAtt | SEQ ID NO: 220 |
| GCACCATGAAGAAGATGATtt | SEQ ID NO: 221 |
| AGAGGATAGTATTAGCCAAtt | SEQ ID NO: 222 |
| CCGATTTCTTCGCTGGAATtt | SEQ ID NO: 223 |
| ACACAGGCCCAGTTTCAAAtt | SEQ ID NO: 224 |
| CCATTTACAGCAGGAGTTAtt | SEQ ID NO: 225 |
| GGACACCCATGAAGCTAATtt | SEQ ID NO: 226 |
| ACAAGGACGAGGACATGTAtt | SEQ ID NO: 227 |
| TGTCCAACCTCATGGCCTTtt | SEQ ID NO: 228 |
| CCTCAGCAGGAGTGACACAtt | SEQ ID NO: 229 |
| GCCAGTACATAGAGGATAGtt | SEQ ID NO: 230 |
| TAATTTAGCTGCTGCCGATtt | SEQ ID NO: 231 |
| CCTATGTATTCCTGATGTTtt | SEQ ID NO: 232 |
| TAACACAGGCCCAGTTTCAtt | SEQ ID NO: 233 |
| CCCATGAAGCTAATGAAGAtt | SEQ ID NO: 234 |
| CAGCCAGTACATAGAGGATtt | SEQ ID NO: 235 |
| GAGGATAGTATTAGCCAAGtt | SEQ ID NO: 236 |
| CTGGAATTGCCTATGTATTtt | SEQ ID NO: 237 |
| TGGAGAGGCACATGTCAATtt | SEQ ID NO: 238 |
| CATAGCAACCTGACCAAAAtt | SEQ ID NO: 239 |
| AGGACACCCATGAAGCTAAtt | SEQ ID NO: 240 |
| TGGCGTGCAGCATGTGAAAtt | SEQ ID NO: 241 |

TABLE 10A-continued

Candidate EDG7 siRNA molecules (sense)

| | |
|---|---|
| ACACTGATACTGTCGATGAtt | SEQ ID NO: 242 |
| GGATAGTATTAGCCAAGGTtt | SEQ ID NO: 243 |
| CGATTTCTTCGCTGGAATTtt | SEQ ID NO: 244 |
| CGATGACTGGACAGGAACAtt | SEQ ID NO: 245 |
| CATACAAGTGGGTCCATCAtt | SEQ ID NO: 246 |
| TAGTATTAGCCAAGGTGCAtt | SEQ ID NO: 247 |
| TCATCGCGGCAGTGATCAAtt | SEQ ID NO: 248 |
| TGAAGACGGTGATGACTGTtt | SEQ ID NO: 249 |

TABLE 10A-continued

Candidate EDG7 siRNA molecules (sense)

| | |
|---|---|
| CTGGACAGGAACAAAGCTTtt | SEQ ID NO: 250 |
| GGTCATCGCGGCAGTGATCtt | SEQ ID NO: 251 |
| GGAGCAACACTGATACTGTtt | SEQ ID NO: 252 |
| CTTCTGGACAGTAGCTTGAtt | SEQ ID NO: 253 |
| GAGAGGCACATGTCAATCAtt | SEQ ID NO: 254 |
| TGACAAGCACATGGACTTTtt | SEQ ID NO: 255 |
| CCCATTTACAGCAGGAGTTtt | SEQ ID NO: 256 |

TABLE 10B

Antagonists for EDG7

| Company | Product | Active Ingredient | Phase | Description |
|---|---|---|---|---|
| Amira Pharmaceuticals (Private) | AM966 | — | PC | AM966 is a LPA1 (lysophosphatidic acid receptor 1) inhibitor. Lysophosphatidic acid receptor 1 (LPAR1; EDG2; LPA1) is an EDG receptor that is part of the phosphatidic acid/lysophosphatidylcholine pathway. Lysophosphatidic acid (LPA) is an anionic bioactive lipid that acts through EDG receptors to mediate cell proliferation, platelet aggregation, smooth muscle contraction, inhibition of neuroblastoma cell differentiation, chemotaxis and tumor cell invasion. LPA also elicits angiogenesis. AM966 is being developed for the treatment of idiopathic pulmonary fibrosis (IPF). |
| Amira Pharmaceuticals (Private) | LPA1 Receptor Antagonist | — | PC | LPA1 Receptor Antagonist acts by blocking the LPA-induced migration of cancer cells and is being developed for the treatment of cancer. |
| Amira Pharmaceuticals (Private) | LPA1 Receptor Antagonist | — | PC | LPA1 Receptor Antagonist is an anti-fibrotic and anti-inflammatory agent which is being developed for the treatment of kidney fibrosis. |
| Catena Pharmaceuticals, Inc. (Private) | VPC51299 | — | PC | VPC51299 is a potent lysophosphatidic acid (LPA1) receptor antagonist which targets LPA G-protein coupled receptors (GPCRs) with high potency. These GPCRs elicit a signaling cascade upon LPA binding the receptor leading to LPA's biological effects, such as proliferation, migration, angiogenesis. VPC51299 antagonizes (blocks) this signaling cascade. VPC51299 is being developed as oral formulation for the treatment of solid tumors. |
| Debiopharm Group (Private) | Debio0719 | — | PC | Debio 0719 is a highly potent, selective, small molecule inhibitor of type 1 lysophosphatidic acid receptor (LPA1) and type 3 (LPA3). Debio 0719 is being developed for the treatment of osteolytic bone damage induced by breast tumour metastasis. |
| Kyowa Hakko Kirin Co., Ltd. (formerly Kyowa Hakko Kogyo Co., Ltd.) (Stock Code Number: 4151 (TYO)) | Debio0719 | — | PC | Debio0719 is a highly potent, selective, small molecule inhibitor of type 1 lysophosphatidic acid receptor (LPA1) and type 3 (LPA3). Debio0719 is being developed for the treatment of bone damage induced by metastatic breast cancer. Note: This product is added upon merger of Kyowa Hakko Kogyo Co., Ltd. with Kirin Pharma Company Limited |
| Amira Pharmaceuticals (Private) | AM152 | — | 1 | AM152 is a lysophosphatidic acid (LPA1) antagonist that acts by blocking phosphatidic acid/lysophosphatidylcholine pathway involved in fibrotic disease and is being developed for the treatment of idiopathic pulmonary fibrosis. |

TABLE 10B-continued

| | Antagonists for EDG7 | | |
|---|---|---|---|
| | Company | Indication | MOA |
| | Amira Pharmaceuticals (Private) | Pulmonary Fibrosis (Idiopathic Pulmonary Fibrosis) | Lysophosphatidic Acid Type 1 Receptor (LPA1) Antagonist |
| | Amira Pharmaceuticals (Private) | Cancer | Lysophosphatidic Acid Type 1 Receptor (LPA1) Antagonist |
| | Amira Pharmaceuticals (Private) | Kidney Disease (Kidney Fibrosis) | Lysophosphatidic Acid Type 1 Receptor (LPA1) Antagonist |
| | Catena Pharmaceuticals, Inc. (Private) | Solid Tumors | Lysophosphatidic Acid Type 1 Receptor (LPA1) Antagonist |
| | Debiopharm Group (Private) | Bone Metastases (Bone Damage Induced by Metastatic Breast Cancer) | Lysophosphatidic Acid Type 1 Receptor (LPA1) Antagonist; Lysophosphatidic Acid Type 3 Receptor (LPA3) Antagonist |
| | Kyowa Hakko Kirin Co., Ltd. (formerly Kyowa Hakko Kogyo Co., Ltd.) (Stock Code Number: 4151 (TYO)) | Bone Metastases (Bone Damage Induced by Metastatic Breast Cancer) | Lysophosphatidic Acid Type 1 Receptor (LPA1) Antagonist; Lysophosphatidic Acid Type 3 Receptor (LPA3) Antagonist |
| | Amira Pharmaceuticals (Private) | Pulmonary Fibrosis (Idiopathic Pulmonary Fibrosis) | Lysophosphatidic Acid Type 1 Receptor (LPA1) Antagonist |

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

What is claimed is:

1. A method of treating Type I Diabetes (T1D) in a human subject, comprising
   a) obtaining a biological sample from said subject, said sample comprising nucleic acid;
   b) determining the presence or absence of a T1D associated single nucleotide polymorphism selected from

| Chr | SNP | Position | Gene | Aff allele freq | Ctrl allele freq | OR [95% CI] | P |
|---|---|---|---|---|---|---|---|
| 21 | rs9976767 | 42709459 | UBASH3A | 0.474 | 0.436 | 1.165 [1.051-1.292] | 0.0036 |
| 9 | rs10758593 | 4282083 | GLIS3 | 0.429 | 0.426 | 1.013 [0.913-1.124] | 0.81 |
| 9 | rs10758594 | 4285583 | GLIS3 | 0.434 | 0.443 | 0.963 [0.869-1.068] | 0.48 |
| 15 | rs8035957 | 36625556 | RASGRP1 | 0.270 | 0.261 | 1.047 [0.932-1.176] | 0.44 |
| 6 | rs3757247 | 91014184 | BACH2 | 0.497 | 0.463 | 1.144 [1.033-1.268] | 0.010 |
| 1 | rs1983853 | 85083780 | EDG7 | 0.132 | 0.153 | 0.842 [0.726-0.976] | 0.022 | and
   c) administering to said human subject a therapeutically effective amount of at least one agent useful for the treatment of T1D symptoms when said SNP is present, wherein said agent is at least one siRNA provided in Tables 6-10 in a pharmaceutically acceptable carrier.

2. The method of claim 1, wherein said symptoms are aberrant blood sugar levels.

3. The method of claim 1, wherein said agent modulates function of a gene product selected from the group consisting of UBASH3A, GLIS3, RASGRP1, BACH2, and EDG7.

4. The method of claim 1, wherein said SNP is determined using a process selected from the group consisting of detection of specific hybridization, measurement of allele size, restriction fragment length polymorphism analysis, allele-specific hybridization analysis, single base primer extension reaction, and sequencing of an amplified polynucleotide.

5. The method of claim 1, further comprising determining the presence or absence of rs17574546 and rs7171171.

* * * * *